(12) United States Patent
Westin et al.

(10) Patent No.: US 11,206,245 B2
(45) Date of Patent: *Dec. 21, 2021

(54) SYSTEMS AND DEVICES FOR ENCRYPTING, CONVERTING AND INTERACTING WITH MEDICAL IMAGES

(71) Applicant: Trice Imaging, Inc., Del Mar, CA (US)

(72) Inventors: Martin Westin, Stockholm (SE); Johanna Wollert Melin, Stockholm (SE); Asa Sjoblom Nordgren, Del Mar, CA (US)

(73) Assignee: TRICE IMAGING, INC., Del Mar, CA (US)

( * ) Notice: Subject to any disclaimer, the term of this patent is extended or adjusted under 35 U.S.C. 154(b) by 285 days.

This patent is subject to a terminal disclaimer.

(21) Appl. No.: 16/570,821

(22) Filed: Sep. 13, 2019

(65) Prior Publication Data

US 2020/0007516 A1    Jan. 2, 2020

Related U.S. Application Data

(63) Continuation of application No. 15/652,101, filed on Jul. 17, 2017, now Pat. No. 10,419,405, which is a
(Continued)

(51) Int. Cl.
*H04L 29/06* (2006.01)
*G16H 30/20* (2018.01)
(Continued)

(52) U.S. Cl.
CPC ........ *H04L 63/0428* (2013.01); *G06F 21/602* (2013.01); *G16H 30/20* (2018.01); *G16H 30/40* (2018.01); *H04L 63/0414* (2013.01)

(58) Field of Classification Search
USPC ........ 713/150, 163, 168, 181; 726/2, 21, 36; 380/255, 264, 276
See application file for complete search history.

(56) References Cited

U.S. PATENT DOCUMENTS 6,440,072 B1    8/2002  Schuman et al.
6,647,157 B1 *  11/2003 Shiiyama ............. G06K 9/4647
                                                          358/403
(Continued)

FOREIGN PATENT DOCUMENTS

CN          1822182 A      8/2006
CN        102713913 A     10/2012
(Continued)

OTHER PUBLICATIONS

Andrade et al., Wireless and PDA: a novel strategy to access DICOM-compliant medical data on mobile devices, International Journal of Medical Informatics, 2003, 7 pages.
(Continued)

*Primary Examiner* — Sharif E Ullah
(74) *Attorney, Agent, or Firm* — Procopio, Cory, Hargreaves & Savitch LLP

(57) ABSTRACT

A network device and a peripheral device for attachment with a medical imaging device provides for the encryption and conversion of a medical image into a secure and standardized image file format as well as the communication of the encrypted and/or converted image to a secure server on a remote network. The devices may detect an unencrypted medical image file transmitted and encrypt and convert selected medical image files associated with the medical data based on standardized medical data format specifications that correlate with an output destination type. An encryption and conversion unit may be incorporated within the hardware and software of a medical imaging device or another network device in order to provide the capability for encrypting a medical image for transmission that is compatible with a destination device or network.

20 Claims, 25 Drawing Sheets

Related U.S. Application Data continuation of application No. 14/571,265, filed on Dec. 15, 2014, now Pat. No. 9,712,498, which is a continuation of application No. PCT/US2013/046027, filed on Jun. 14, 2013, which is a continuation of application No. 12/904,867, filed on Oct. 14, 2010, now Pat. No. 9,087,080.

(60) Provisional application No. 61/659,957, filed on Jun. 14, 2012, provisional application No. 61/659,958, filed on Jun. 14, 2012, provisional application No. 61/659,959, filed on Jun. 14, 2012, provisional application No. 61/659,972, filed on Jun. 14, 2012, provisional application No. 61/659,971, filed on Jun. 14, 2012, provisional application No. 61/251,334, filed on Oct. 14, 2009.

(51) Int. Cl.
*G16H 30/40* (2018.01)
*G06F 21/60* (2013.01)

(56) References Cited

U.S. PATENT DOCUMENTS

| | | | |
|---|---|---|---|
| 7,116,807 B1 | 10/2006 | Brackett | |
| 7,196,718 B1* | 3/2007 | Barbeau | H04N 7/147 348/14.01 |
| 7,613,478 B2 | 11/2009 | Jabri et al. | |
| 7,953,614 B1 | 5/2011 | Reicher et al. | |
| 8,108,432 B2* | 1/2012 | Westin | G16H 30/20 707/792 |
| 9,760,677 B2 | 9/2017 | Yu | |
| 2001/0016056 A1 | 8/2001 | Westphal et al. | |
| 2001/0051881 A1* | 12/2001 | Filler | G16H 15/00 705/3 |
| 2002/0016718 A1 | 2/2002 | Rothschild et al. | |
| 2002/0016922 A1 | 2/2002 | Richards | |
| 2002/0091659 A1 | 7/2002 | Beaulieu et al. | |
| 2003/0055686 A1 | 3/2003 | Satoh et al. | |
| 2003/0081234 A1 | 5/2003 | Wiley | |
| 2003/0140141 A1 | 7/2003 | Mullen et al. | |
| 2003/0182139 A1 | 9/2003 | Harris et al. | |
| 2003/0206646 A1 | 11/2003 | Brackett | |
| 2004/0073571 A1 | 4/2004 | Kumhyr | |
| 2004/0075433 A1 | 4/2004 | Kaufman | |
| 2004/0078238 A1 | 4/2004 | Thomas et al. | |
| 2004/0111531 A1 | 6/2004 | Staniford et al. | |
| 2004/0114172 A1* | 6/2004 | Ohyama | H04N 1/00236 358/1.13 |
| 2004/0184643 A1* | 9/2004 | Stantchev | G16H 40/63 382/128 |
| 2005/0021642 A1 | 1/2005 | Nonaka | |
| 2005/0068577 A1 | 3/2005 | Birkhoelzer et al. | |
| 2005/0071434 A1 | 3/2005 | Hettish | |
| 2005/0080330 A1 | 4/2005 | Masuzawa et al. | |
| 2005/0086240 A1 | 4/2005 | Richardson et al. | |
| 2005/0131997 A1 | 6/2005 | Lewis et al. | |
| 2005/0226408 A1* | 10/2005 | Hotz | H04L 9/0662 380/28 |
| 2006/0008130 A1 | 1/2006 | Yamamichi | |
| 2006/0034538 A1 | 2/2006 | Potter et al. | |
| 2006/0056680 A1 | 3/2006 | Stutsman | |
| 2006/0077940 A1 | 4/2006 | Ganji | |
| 2006/0115135 A1 | 6/2006 | Dehmeshki et al. | |
| 2006/0117378 A1 | 6/2006 | Tam et al. | |
| 2006/0155577 A1* | 7/2006 | Niemeyer | G16H 30/40 705/2 |
| 2006/0168338 A1* | 7/2006 | Bruegl | H04L 29/08729 709/240 |
| 2006/0184672 A1* | 8/2006 | Lauer | H04L 67/1097 709/225 |
| 2006/0190742 A1* | 8/2006 | Ebitani | G06F 21/602 713/193 |
| 2006/0235871 A1* | 10/2006 | Trainor | G06F 16/38 |
| 2006/0239394 A1 | 10/2006 | Fujieda | |
| 2006/0282447 A1 | 12/2006 | Hollebeek | |
| 2007/0055538 A1 | 3/2007 | Burton | |
| 2007/0064703 A1 | 3/2007 | Hernandez et al. | |
| 2007/0099605 A1 | 5/2007 | Shanahan | |
| 2007/0118540 A1 | 5/2007 | Guo | |
| 2007/0168461 A1 | 7/2007 | Moore | |
| 2007/0192138 A1* | 8/2007 | Saito | G16H 10/60 705/3 |
| 2007/0192140 A1 | 8/2007 | Gropper | |
| 2007/0299853 A1 | 12/2007 | Knotz et al. | |
| 2008/0016244 A1 | 1/2008 | Noonan et al. | |
| 2008/0021730 A1 | 1/2008 | Holla et al. | |
| 2008/0021741 A1 | 1/2008 | Holla et al. | |
| 2008/0027974 A1 | 1/2008 | Collins | |
| 2008/0052112 A1* | 2/2008 | Zahlmann | G16H 30/40 705/2 |
| 2008/0059245 A1* | 3/2008 | Sakaida | G16H 30/40 705/3 |
| 2008/0109250 A1 | 5/2008 | Walker et al. | |
| 2008/0141107 A1 | 6/2008 | Catallo et al. | |
| 2009/0112882 A1 | 4/2009 | Maresh et al. | |
| 2009/0164253 A1 | 6/2009 | Lyshkow | |
| 2009/0164504 A1 | 6/2009 | Flake et al. | |
| 2009/0165504 A1 | 7/2009 | Kim | |
| 2009/0245573 A1 | 10/2009 | Saptharishi et al. | |
| 2009/0287505 A1 | 11/2009 | Wood | |
| 2009/0292559 A1 | 11/2009 | Ranjan et al. | |
| 2009/0327246 A1 | 12/2009 | Sato | |
| 2010/0082370 A1 | 4/2010 | Frederick et al. | |
| 2010/0094700 A1 | 4/2010 | Kuth et al. | |
| 2010/0115288 A1 | 5/2010 | Monk et al. | |
| 2010/0246981 A1 | 9/2010 | Hu et al. | |
| 2010/0250497 A1 | 9/2010 | Redlich | |
| 2011/0110568 A1 | 5/2011 | Vesper et al. | |
| 2011/0130119 A1* | 6/2011 | Gupta | H04L 9/3226 455/411 |
| 2011/0138269 A1* | 6/2011 | Cordonnier | G16H 10/60 715/239 |
| 2011/0161450 A1 | 6/2011 | Westin et al. | |
| 2012/0041786 A1 | 2/2012 | Yu | |
| 2012/0143625 A1* | 6/2012 | Eaves | G16H 10/60 705/3 |
| 2012/0179670 A1* | 7/2012 | Burke | G06F 16/583 707/722 |
| 2013/0021635 A1 | 1/2013 | Wright et al. | |
| 2013/0097086 A1* | 4/2013 | Dala | G16H 80/00 705/51 |
| 2014/0142983 A1 | 5/2014 | Backhaus et al. | |
| 2014/0152466 A1 | 6/2014 | Wiesner et al. | |

FOREIGN PATENT DOCUMENTS

| | | |
|---|---|---|
| JP | 2005176314 A | 6/2005 |
| JP | 2006320714 A | 11/2006 |
| KR | 1020070022975 A | 2/2007 |
| KR | 1020090053039 A | 5/2009 |
| WO | 2008011063 A2 | 1/2008 |
| WO | 2013188850 A1 | 12/2013 |

OTHER PUBLICATIONS

Banitsas et al., Using handheld devices for real-time wireless Teleconsultation, International Conference of the IEEE EMBS, 2004, 4 pages.

Chinese Office Action received in related Chinese Patent Application No. 201080056632.X, dated Aug. 5, 2014, 49 pages including translation.

Chinese Office Action received in related Chinese Patent Application No. 201080056632.X, dated Jul. 6, 2015, 48 pages including translation.

European Search Report received in related European Patent Application No. 10824126.6, dated Nov. 13, 2014, 7 pages.

Examination report for related EP Patent Application No. 10824126.6, dated Jun. 28, 2018, in 3 pages.

(56) References Cited

OTHER PUBLICATIONS

Examination report for related EP Patent Application No. 10824126.6, dated Mar. 6, 2019, in 4 pages.
Examination report for related EP Patent Application No. 10824126.6, dated Nov. 6, 2017, in 5 pages.
Examination report for related EP Patent Application No. 15850895.2, dated Jun. 18, 2019, in 11 pages.
Extended European Search Report received in related European patent application No. 13804775.8, dated Jan. 15, 2016, 8 pages.
Extended European Search Report received in related European patent application No. 15850895.2, dated Jun. 5, 2018, 8 pages.
International Search Report and Written Opinion issued in International Patent Application No. PCT/US2010/052746 dated May 30, 2011 (10 pages).
International Search Report and Written Opinion received in related PCT Application No. PCT/US2013/046027, dated Aug. 28, 2013, 15 pages.
International Search Report and Written Opinion received in related PCT Application No. PCT/US2015/055832, dated Jan. 29, 2016, 11 pages.
Office Action for related KR Patent Application No. 10-2012-7012310, dated Dec. 9, 2016, in 18 pages.
Office Action for related KR Patent Application No. 10-2012-7012310, dated Oct. 27, 2017, in 8 pages.
Raman et al., Radiology on Handheld Devices: Image Display, Manipulation, and PACS Integration Issues, RadioGraphics, vol. 24, No. 1, 2004, 12 pages.
Tang. "A Mobile Phone Integrated Health Care Delivery System of Medical Images." PMC, Aug. 2004.
Third Chinese Office Action received in related Chinese patent application No. 201080056632.X, dated Feb. 5, 2016, English translation 3 pages, original Office Action 3 pages.
Lim et al. "Development of an electronic medical report delivery system to 3G GSM mobile (cellular) phones for a medical imaging department." Annual International Conference of the IEEE Engineering in Medicine and Biology Society. Jan. 1, 2007 p. 6726-6729. Retrieved from the Internet: http://www.ncbi.nlm.nih.gov/pubmed/18003570.
Notification of Grounds for Refusal received in co-pending Korean patent application No. 10-2012-7012310, dated Dec. 9, 2016, 18 pages.
Branstetter et al. "Practical Imaging Informatics." Springer Science. 2009. 450 pages.
Merge Healthcare, "eFilm Scan™ 2.0 User Guide," https://estore.merge.com/na/resources/eScan20userguidepdf; Mar. 27, 2008. 55 pages.
Notice of Allowance dated Jul. 9, 2020 for related U.S. Appl. No. 15/882,487 in 12 pages.
Office Action dated May 21, 2020 for related U.S. Appl. No. 15/882,487 in 27 pages.
Summons to Attend Oral Proceedings dated Apr. 6, 2020 for related EP Patent Application No. 15850895.2, in 14 pages.
Lei, Zhenjia. "Authentication Based on Shared Key." Computer Network (Third Edition). Apr. 30, 2011. 3 pages.
Office Action (with English translation) for related CN Patent Application No. 201580067622.9, dated Aug. 31, 2020, in 25 pages.
Office Action and Search Report for related CN Patent Application No. 201580067622 9, dated Feb. 3, 2020, in 21 pages (with translation).
Office Action dated Mar. 4, 2020 for related U.S. Appl. No. 15/976,069 in 26 pages.

\* cited by examiner

Typical Flow for Primary Care

FIG. 18
Dashboard

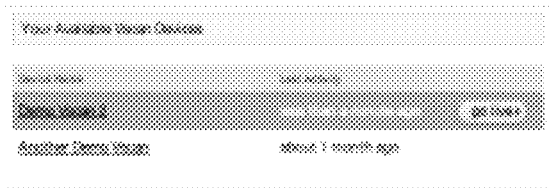

List of available Vscan devices
Each user can have one or more Vscan devices. They are shown on the dashboard ordered by recent activity.

When the application receives a new Exam from a Vscan it will be highlighted and moved to the top of the list.

Additionally an alert will go out via SMS and Email to an "on-call" user assigned to that device.

Searching for Patients
The dashboard also contains a seach field where patients can be found by searching by name, birthdate, id and similar information.

FIG. 19

Main Menu

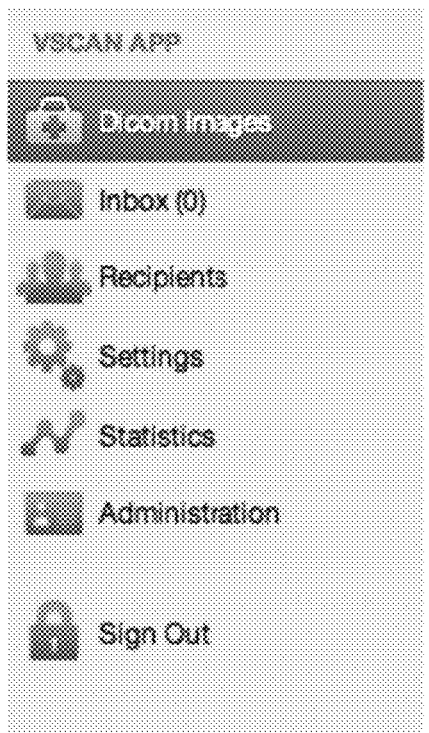

Dicom Images is where we will be spending most of our time. It contains the main image workflows which we'll cover in this document.

Inbox (n) contains internal messages you have received in relation to diagnosis cases.

Recipients are patients of other external contacts that are saved for easy access when sending images or studies.

Settings handle setup of Vscan devices, Anonymization, Automation of patient messages and labels to categorize studies.

Statistics shows traffic through the application over time.

Administration is where administrators manage user accounts and setup branding of patient images.

Account is where non-admins edit their account details.

Sign Out does just that. Signs you out.

FIG. 24

Requesting a Diganosis

Clicking "Send for Diagnosis" on the Study page will show a form where you can select one or more concerns you wish to have investigated.

You also write a free-text message, similar to an email message, explaining the case and your request in more detail.

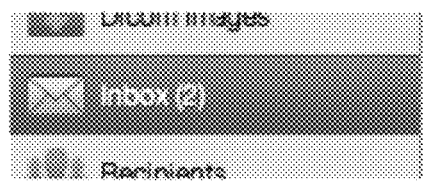

When you send a study for diagnosis it will inform the receiving doctor via email and add a message to his/her inbox in the application.

Similarly when a reply is generated it will show up in your inbox. Both email and in the app.

Making a Diganosis

SYSTEMS AND DEVICES FOR ENCRYPTING, CONVERTING AND INTERACTING WITH MEDICAL IMAGES

The present application is a continuation of U.S. patent application Ser. No. 15/652,101, filed Jul. 17, 2017, which is a continuation of U.S. patent application Ser. No. 14/571,265, filed Dec. 15, 2014, now U.S. Pat. No. 9,712,498, which is a continuation of PCT/US2013/046027, filed Jun. 14, 2013, which claims the benefit of the priority of U.S. Provisional Application Nos. 61/659,957, filed Jun. 14, 2012, 61/659,958, filed Jun. 14, 2012, 61/659,959, filed Jun. 14, 2012, 61/659,972, filed Jun. 14, 2012, and 61/659,971 filed Jun. 14, 2012 the disclosures of which are incorporated herein by reference in their entirety. U.S. patent application Ser. No. 14/571,265 is also a continuation of U.S. patent application Ser. No. 12/904,867, filed Oct. 14, 2010, now U.S. Pat. No. 9,087,080, which claims the benefit of U.S. Provisional Application No. 61/251,334, filed Oct. 14, 2009.

BACKGROUND

1. Technical Field

The embodiments described herein are related to delivery of medical image records, and more particularly to the automatic encryption and conversion of medical image files for delivery to mobile devices and/or remote communication systems.

2. Related Art

Medical diagnostic devices and medical imaging systems have become increasingly complex in recent years. In response to the increasing challenges in digital imaging technology, the American College of Radiology (ACR) and the National Electrical Manufacturers Association (NEMA) developed the Digital Imaging and Communications in Medicine (DICOM) standard. DICOM is a standard for handling, storing, printing, and transmitting information in medical imaging. It includes a file format definition and a network communication protocol. The network communication protocol is an application protocol that uses TCP/IP to communicate between systems. One of the goals of the standard is to make uniform the transferring of medical images and information between viewing and scanning sources to allow users of different imaging software and/or hardware to share information. DICOM files can be exchanged between two entities that are capable of receiving image and patient data in DICOM format. DICOM enables the integration of scanners, servers, workstations, printers, and network hardware from multiple manufacturers into a Picture Archiving and Communication System (PACS) for storing and downloading of digital images. The different devices come with DICOM conformance statements that clearly state the DICOM classes they support. DICOM has been widely adopted by hospitals, and is gaining popularity in smaller dentists' and doctors' offices.

DICOM files commonly contain images; therefore, they are often referred to as DICOM images. But it will be understood that a DICOM file does not necessarily need to include an image. Rather, such a file can include measurements or report data. Thus, DICOM files may contain media data, such as, video and audio data, or no media data at all. In that case, DICOM files may contain only metadata identifying the originating modality, the operator, or the patient being examined. Modality here refers to any image generating equipment in medical imaging, such as, Ultrasound (US), Magnetic Resonance Imaging (MRI), Computed Tomography (CT), Positron Emission Tomography (PET), radiographs, and the like.

The type of data and amount of data available in any one DICOM image file varies. A DICOM file is generally structured using data identifying Patient, Study, Series and Instance in that hierarchical order. A Patient can be involved in a number of Studies (cases), which in turn may contain a number of Series (examination or visits), which in turn may contain a number of Instances (files usually containing images). It means that a DICOM file can be unambiguously identified and fitted into that hierarchy. All DICOM files contain an identifier for the generating modality. In other words, the identifier will reflect the equipment or location in which the file was originated. The files also contain timestamps pertaining to both the file itself (Instance) and the Series. Using the timestamps and the originating identifier, an image can be unambiguously identified using that data without involving any identifiable patient information to safeguard patient privacy issues. In addition, DICOM file format differs from other data formats in that it groups information into data sets. For example, a file of a chest X-Ray image actually contains the patient ID within the file, so that the image can never be separated from this information by mistake.

Most PACSs handle images from various medical imaging instruments, including US, MM, PET, CT, and the like. Electronic images and reports are transmitted digitally via PACS; this eliminates the need to manually file, retrieve or transport film jackets. A PACS consists of four major components: the imaging modalities, such as, CT and Mill; a secured network for the transmission of patient information; workstations for interpreting and reviewing images; and long and short term archives for the storage and retrieval of images and reports. Combined with available and emerging Web technology, PACS has the ability to deliver timely and efficient access to images, interpretations and related data. PACS breaks down the physical and time barriers associated with traditional film-based image retrieval, distribution and display.

Medical imaging devices typically output digital image data. The overwhelming majority, if not all, of such devices use the DICOM standard for both image file format and network transfers. These images are generally not readable by consumer image viewers or mobile devices. Therefore, patients who wish to share their medical images struggle with conversion and delivery of these images. A good example is to share images from an Ultrasound examination during a pregnancy. The future parents usually would like to keep, share and display the images of their future child. They might also conceivably want to send these images to their friends' and relatives' cellular phones or email accounts. They might even want to post them on a social network, or they might just want to keep them in their personal digital "photo album". All of these events would require them to either scan a printed hard-copy of the image, or to find, purchase, install and learn to use DICOM viewer software package with export capabilities. These software packages are usually not readily available or they are not economical for limited use.

It should also be noted that this issue is not necessarily limited to DICOM files. In general, there is no real method for a patient to view images related to their condition, treatment, status, etc. Moreover, there are few, if any effective means by which a doctor or clinician can quickly and remotely retrieve images for diagnostic or other purposes.

In fact, many smaller medical practices, such as, small clinics, doctors' offices, and dentists' offices also suffer from an inability to convert, deliver, and receive medical images economically and timely. These facilities usually do not have the technical support-staff or finances to run a full PACS for image archiving and delivery to remote expert doctors for second opinions and consultations. They often resort to using films, or writable CDs which are sent by mail or messenger. This is both slow, environmentally unfriendly and, in the case of using unregistered postal delivery, insecure. The cost of running a PACS is not just paying the licensing fees. Major investments in advanced infrastructure including the surrounding software, hardware, and facility, as well as the cost for educating staff, and the hours spent on administration will add to the cost of running a PACS. These major investments are expensive, therefore, usually out-of-reach for most small businesses.

Additionally, many medical practices may not have a local network where medical imaging equipment communicates, or the local network may not be secure or properly configured to receive and communicate medical images. The medical imaging devices themselves often lack the capability to encrypt or convert the captured images. The local network, if it does exist, may be incapable of incorporating network devices such as a PACS for the management of digital images.

SUMMARY

A peripheral device for attachment with a medical imaging device provides for the encryption and conversion of a medical image into a secure and standardized image file format as well as the communication of the encrypted and/or converted image to a secure server on a remote network.

According to one aspect, a peripheral encryption and conversion device comprises a communication interface which receives a medical image file, the medical image file comprising medical data and meta data, the medical data having a medical data format; a conversion unit which converts the medical data format associated with the medical data based on standardized format specifications that correlate with an output destination type to create a converted medical image file; an encryption unit which encrypts the converted medical image file to create an encrypted medical image file; and a transmission unit which transmits the encrypted medical image file.

According to one aspect, a system for automated conversion and delivery of medical images, comprising: a communication interface; a data storage system configured to store a plurality of medical images, meta data associated with the plurality of medical images, converted medical images, a plurality of standardized format specifications for a plurality of destination devices and services, and a plurality of message templates; a server coupled with the data storage system and the communication interface, the server configured to: receive a medical image file via the communications interface, the medical image file comprising medical data and meta data, the medical data having a medical data format that complies with the digital imaging and communication in medicine standard, determine whether the medical data includes a medical image data, determine an output destination type, wherein the output destination type is an output device, service, or both, based on the meta data, correlate the output destination type with one or more of the plurality of standardized format specifications and with one or more of the plurality of message templates, convert the medical data format associated with the medical data based on the standardized format specifications that correlate with the output destination type, assemble at least one output message that includes the converted medical data based on the message templates that correlate with the output destination type, and transmit the output message to at least one destination via the communication interface.

According to another aspect, a method for automated conversion and delivery of medical images, comprising: storing a plurality of medical images, meta data associated with the plurality of medical images, converted medical images, a plurality of standardized format specifications for a plurality of destination devices and services, and a plurality of message templates; receiving a medical image file via a communications interface, the medical image file comprising medical data and meta data, the medical data having a medical data format; determining whether the medical data includes a medical image data; determining an output destination type, wherein the output destination type is an output device, service, or both, based on the meta data; correlating the output destination type with one or more of the plurality of standardized format specifications and with one or more of the plurality of message templates; converting the medical data format associated with the medical data based on the standardized format specifications that correlate with the output destination type; assembling at least one output message that includes the converted medical data based on the message templates that correlate with the output destination type; and transmitting the output message to at least one destination via the communication interface.

A network device may be implemented on a local network to receive medical images from one or more medical imaging devices and convert and encrypt the medical images into a secure and standardized image file format, as well as communicate the encrypted and/or converted image to a secure server on a remote network.

According to one aspect, a network encryption and conversion device comprises a communication interface which receives a medical image file from at least one medical imaging device, the medical image file comprising medical data and meta data, the medical data having a medical data format; a conversion unit which converts the medical data format associated with the medical data based on standardized format specifications that correlate with an output destination type to create a converted medical image file; an encryption unit which encrypts the converted medical image file to create an encrypted medical image file; and a transmission unit which transmits the encrypted medical image file to a remote device on a remote network.

According to one aspect, a system for automated conversion and delivery of medical images, comprising: a communication interface; a data storage system configured to store a plurality of medical images, meta data associated with the plurality of medical images, converted medical images, a plurality of standardized format specifications for a plurality of destination devices and services, and a plurality of message templates; a server coupled with the data storage system and the communication interface, the server configured to: receive a medical image file via the communications interface, the medical image file comprising medical data and meta data, the medical data having a medical data format that complies with the digital imaging and communication in medicine standard, determine whether the medical data includes a medical image data, determine an output destination type, wherein the output destination type is an output device, service, or both, based on the meta data, correlate the output destination type with one or more of the plurality of standardized format specifications and with one or more of the plurality of message templates, convert the medical data format associated with the medical data based on the standardized format specifications that correlate with the output destination type, assemble at least one output message that includes the converted medical data based on the message templates that correlate with the output destination type, and transmit the output message to at least one destination via the communication interface.

According to another aspect, a method for automated conversion and delivery of medical images, comprising: storing a plurality of medical images, meta data associated with the plurality of medical images, converted medical images, a plurality of standardized format specifications for a plurality of destination devices and services, and a plurality of message templates; receiving a medical image file via a communications interface, the medical image file comprising medical data and meta data, the medical data having a medical data format; determining whether the medical data includes a medical image data; determining an output destination type, wherein the output destination type is an output device, service, or both, based on the meta data; correlating the output destination type with one or more of the plurality of standardized format specifications and with one or more of the plurality of message templates; converting the medical data format associated with the medical data based on the standardized format specifications that correlate with the output destination type; assembling at least one output message that includes the converted medical data based on the message templates that correlate with the output destination type; and transmitting the output message to at least one destination via the communication interface.

Systems and methods for encrypting and converting medical image files on a device within a network are provided. An encryption and conversion unit may be incorporated within the hardware and software of a medical imaging device or another network device in order to provide the capability for encrypting a medical image for transmission to a remote network and for converting the medical image to a format that is compatible with a destination device or network. The encryption and conversion unit may also be configured to package and transmit a converted and encrypted image to an appropriate destination, such as a secure server, on a remote network.

According to one aspect, a system for converting and encrypting a medical image comprises a medical imaging device which captures at least one medical image file; the medical imaging device comprising: a communication interface which receives the medical image file from the medical imaging device, the medical image file comprising medical data and meta data, the medical data having a medical data format; a conversion unit which converts the medical data format associated with the medical data based on standardized format specifications that correlate with an output destination type to create a converted medical image file; an encryption unit which encrypts the converted medical image file to create an encrypted medical image file; and a transmission unit which transmits the encrypted medical image file to at least one destination via the communication interface.

According to one aspect, a system for automated conversion and delivery of medical images, comprising: a communication interface; a data storage system configured to store a plurality of medical images, meta data associated with the plurality of medical images, converted medical images, a plurality of standardized format specifications for a plurality of destination devices and services, and a plurality of message templates; a server coupled with the data storage system and the communication interface, the server configured to: receive a medical image file via the communications interface, the medical image file comprising medical data and meta data, the medical data having a medical data format that complies with the digital imaging and communication in medicine standard, determine whether the medical data includes a medical image data, determine an output destination type, wherein the output destination type is an output device, service, or both, based on the meta data, correlate the output destination type with one or more of the plurality of standardized format specifications and with one or more of the plurality of message templates, convert the medical data format associated with the medical data based on the standardized format specifications that correlate with the output destination type, assemble at least one output message that includes the converted medical data based on the message templates that correlate with the output destination type, and transmit the output message to at least one destination via the communication interface.

According to another aspect, a method for automated conversion and delivery of medical images, comprising: storing a plurality of medical images, meta data associated with the plurality of medical images, converted medical images, a plurality of standardized format specifications for a plurality of destination devices and services, and a plurality of message templates; receiving a medical image file via a communications interface, the medical image file comprising medical data and meta data, the medical data having a medical data format; determining whether the medical data includes a medical image data; determining an output destination type, wherein the output destination type is an output device, service, or both, based on the meta data; correlating the output destination type with one or more of the plurality of standardized format specifications and with one or more of the plurality of message templates; converting the medical data format associated with the medical data based on the standardized format specifications that correlate with the output destination type; assembling at least one output message that includes the converted medical data based on the message templates that correlate with the output destination type; and transmitting the output message to at least one destination via the communication interface.

Systems and methods for integrating a variety of communication protocols and file types relating to medical imaging are provided.

According to one aspect, a system for automated conversion and delivery of medical images, comprising: a communication interface; a user interface; a data storage system configured to store a plurality of medical images, meta data associated with the plurality of medical images, converted medical images, a plurality of standardized format specifications for a plurality of destination devices and services, and a plurality of message templates; a server coupled with the data storage system and the communication interface, the server configured to: receive a plurality of medical image files via the communications interface, the medical image files comprising medical data and meta data, the medical data having a medical data format, store the medical image files, receive a request via the user interface to find a medical image file, return a notification that the requested medical image file has been found via the user interface, receive an output destination type associated with the medical data file via the user interface, wherein the output destination type is an output device, service, or both, retrieve the requested medical image file, determine whether the medical data associated with the requested medical image file includes medical image data, correlate the output destination type with one or more of the plurality of standardized format specifications and with one or more of the plurality of message templates, convert the medical data format associated with the medical data based on the standardized format specifications that correlate with the output destination type, assemble at least one output message that includes the converted medical data based on the message templates that correlate with the output destination type, and transmit the output message to at least one destination via the communication interface.

These and other features, aspects, and embodiments are described below in the section entitled "Detailed Description."

BRIEF DESCRIPTION OF THE DRAWINGS

Features, aspects, and embodiments are described in conjunction with the attached drawings, in which:

FIG. 18 illustrates a user interfaces which users of the real-time remote interaction system will view.

FIG. 19 illustrates a user interfaces which users of the real-time remote interaction system will view.

FIG. 24 illustrates a user interfaces which users of the real-time remote interaction system will view.

DETAILED DESCRIPTION

Figure 1:
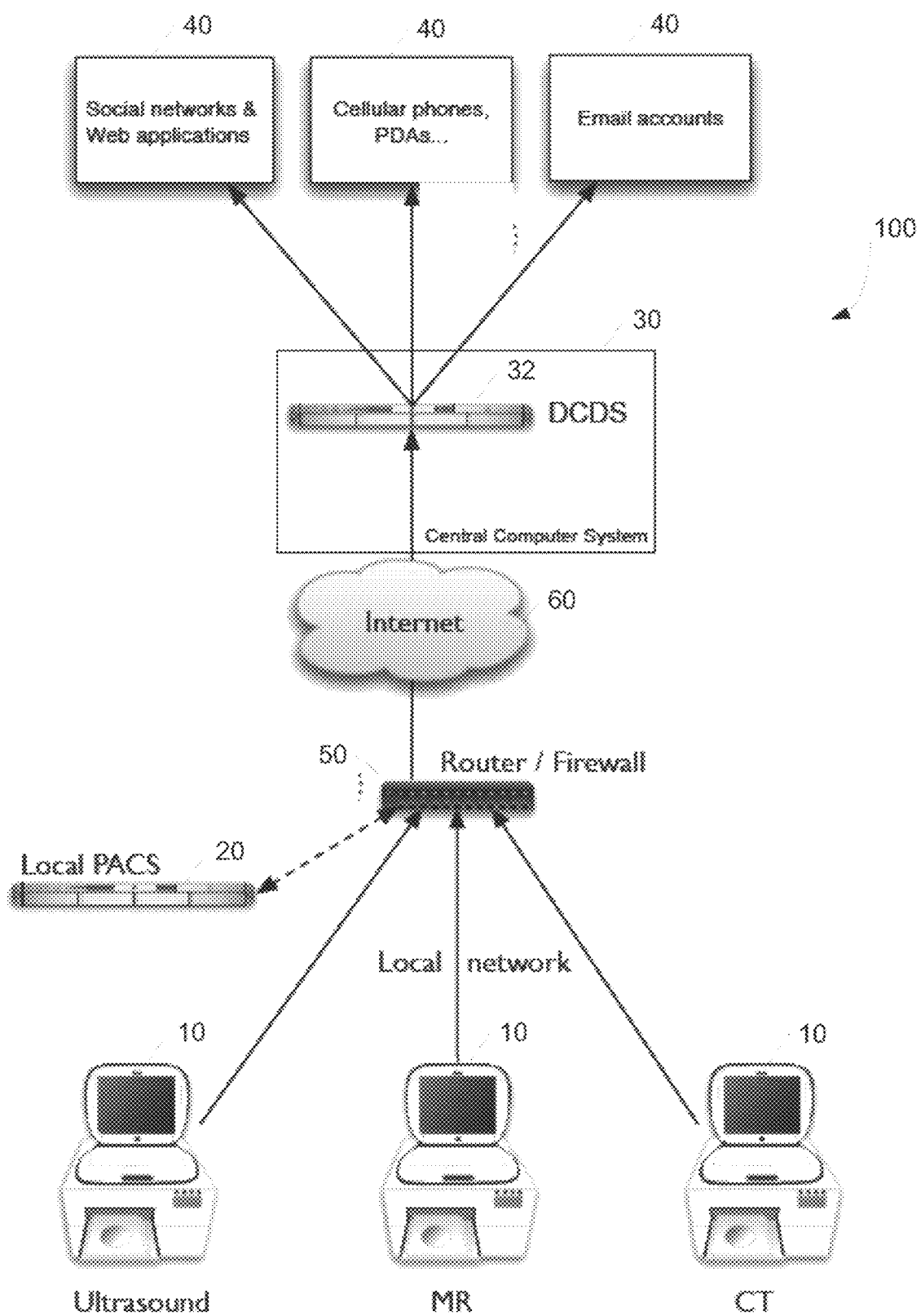
FIG. 1 is a diagram illustrating an example system for the automatic conversion and distribution of medical images to any of a plurality of output modalities in accordance with one embodiment.

FIG. 1 is a diagram illustrating an example system 100 for the automatic conversion and distribution of medical images to any of a plurality of output modalities. The term output modality is used to refer to various types of devices, systems, and services, several examples of which are provided below. As can be seen, system 100 can comprise a plurality of source medical imaging modalities 10, such as Ultrasound, MRI, CT and PET equipment, a local PACS 20 (typically source image archive-servers), or any other device capable of sending medical data such as DICOM data, commonly medical images. Modalities 10 and PACS 20 can be connected, e.g., with a Central Computer System (CCS) 30 via the Internet 60 through a router 50 usually provided with encryption and firewall protection.

Central Computer System (CCS) 30 can include a data conversion and delivery system (DCDS) 32 for processing the medical data. The CCS can comprise one or more servers, and include one or more a processors or CPUs, memory associated with the processor(s), a data storage module, a display means, and an input/output interface means. It should be appreciated that various other peripheral devices and modules can be connected to the CCS, such as other servers, other data storage modules, or intrusion detection systems. The CCS can also be a cluster of interoperating servers, each taking care of a specific task within the system. Similarly, all the modules shown in FIG. 2, and described below can each be a separate server in such a cluster, so as to distribute the load and increase the capacity of the system.

DCDS 32 can be configured to convert medical images associated with the medical data into, e.g., consumer-friendly images, video, or both. DCDS 32 can then in turn send these converted images to a number of destinations, or output modalities 40 as directed by the user/operator of DCDS 32 or as dictated by information included in the medical data. These destinations 40 can be, for example, a web site such as a social networking site including, e.g., Twitter, Facebook, and Google Health; cellular phones; PDAs; Email accounts; or any computer system capable of accepting data via protocols such as, e.g., SOAP and REST. DCDS 32 functions in such a way that it allows source modalities (10, 20) to be protected by the most rigorous of firewall settings 50, while still allowing transfers to take place over the internet 60. The original source image data may optionally be sent to the destinations 40 without any processing or conversion.

For example, when a patient undergoes an ultrasound examination during pregnancy, the ultrasound images can be sent to DCDS 32 for conversion into a set of images that can be sent the parent's social networking web page, their mobile device, their friends and families devices or web pages, etc. More specifically, a nice sequence of the fetus waving its arm can be captured and stored during the ultrasound examination by the operator. The ultrasound operator, usually a nurse or technician, sends the stored, e.g., DICOM file to DCDS 32. The nurse, technician or any trusted employee at the patient's facility (user) can use a remote graphical user interface (GUI) interfaced with DCDS 32 to bring up the desired sequence sent by the source modality 10. The user can then enter the cellular phone numbers, web account information, email addresses, etc., as well as any personal message that the patient indicates, and then start the delivery process. The, e.g., DICOM file, now converted into a cellular phone compatible video format, e.g., 3 gpp, can then be sent as a multimedia message to the mobile phones, and files converted to other appropriate formats can also be sent to the given email and web accounts.

Alternatively, the nurse or technician at the patient's facility can enter the patient's cellular phone number in the patient information field on the ultrasound machine. On receiving the, e.g., DICOM data file, DCDS 32 can be configured to then locate that number embedded in the DICOM data file, and automatically forward the converted image or video file after processing to the desired locations as specified by the patient. Examples of these processes are described in detail below.

Figure 2:
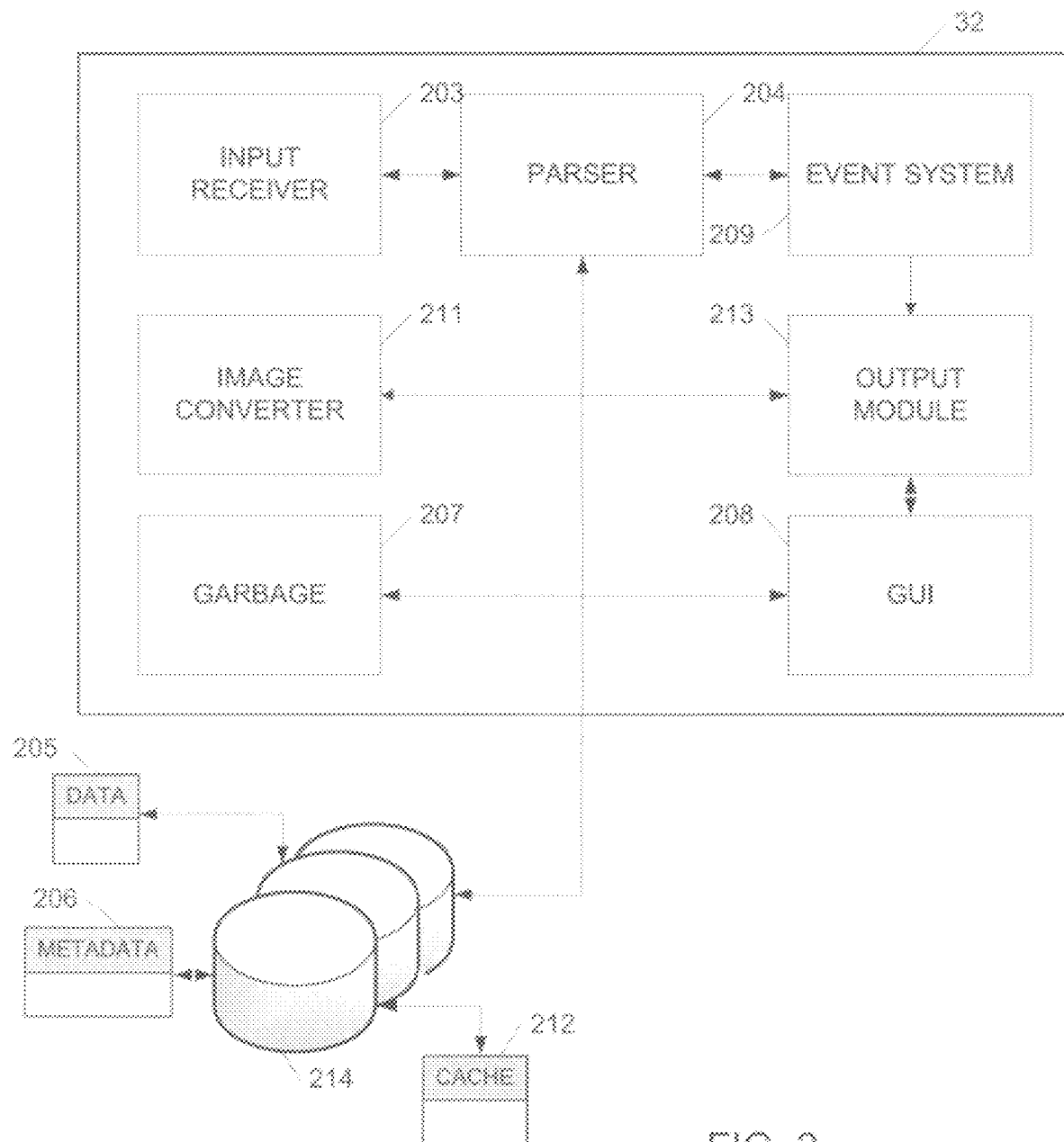
FIG. 2 is a high level block diagram illustrating certain components of an example data conversion and delivery system that can be included in the system of FIG. 1 in accordance with one embodiment.

FIG. 2 is a high level block diagram illustrating certain components of an example DCDS 32 in accordance with one embodiment. It will be understood that the diagram of FIG. 2 is for purposes of explanation and illustration and is not intended to restrict the embodiments described herein to any particular architecture or design. Nor is FIG. 2 intended to provide a detail view of all components of an example DCDS 32. In operation, a request from a modality 10 can be handled by an input stage, consisting of a Receiver 203 and Storage & Parser 204. The Receiver 203 can be configured to authenticate the connection from the source modality 10, and to handle the network transactions necessary to complete the request.

Storage & Parser 204 can be configured to parse the received data and to store any image data 205 and all metadata 206 in storage system 214. For example, the image data 205 can be stored as binary data, while the metadata can be stored as structured data allowing typical structured access to the data, such as, searches and associations between different items. Storage & Parser 204 can be configured in certain implementations or under certain conditions to strip all sensitive patient information from the incoming data file. For example, an operator of the system can use a Graphical User Interface (GUI), such as a Web GUI 208 to selectively set the parts of metadata that are considered to be sensitive. Alternatively, the system can be programmed to automatically determine which fields in the meta data are sensitive. This process is called anonymization, and it is performed in order to protect the patient's privacy. Anonymization is discussed in more detail below.

In certain embodiments, an event signal can be triggered indicating that the newly stored data has been added. When Event System module 209 receives an event signal from the parser 204, it can be configured to determine what action, if any, should be taken as a result. For example, if rules for automatic delivery have been set, and the appropriate metadata values are found in the newly received data stored in structured database 206, then Event System module 209 can be configured to signal the Output Module 213 to send the converted data as instructed by the automatic delivery rules. This process is also described in more detail below.

Output Module 213 can be configured to accept calls from other parts of DCDS 32 containing general data, information to send, and number of delivery destinations, including email addresses. For example, the data can include a text message, a reference to a, e.g., DICOM image, two cellular phone numbers, and one email address. The Output Module 213 can be configured to assemble the appropriate formatted output "packages", or messages, and send the resulting messages using a modular plug-in-based architecture. A plug-in (not shown) for each corresponding type of destination can be included and used by Output Module 213.

In the example provided above, when a service call is received by DCDS 32, Output Module 213 can assemble one MMS message packet containing a jpeg version of an image and message text, all combined and encoded according to the MIMS specifications. This message can then be sent twice, first to each phone number destinations requested, and secondly, to each email address destinations specified.

Output Module 213 can request a converted image from Image Converter 211, identifying the original image and specifying the requested format and dimensions. Image Converter 211 can be configured to then look for an existing image in the Converted Image Cache 212 that matches the request. If no match is found, it can generate an image from the original image data 205. The Image Converter 211 can be configured to use the metadata 206 of the original image stored in database to determine if the requested format is appropriate. If not, it can respond with an error. For example, requesting an mp3 audio version of a still image would result in an error, while requesting a jpeg still image of a multi-frame DICOM image file (effectively video) would be proper.

Image Converter 211 can be configured to respond to an event from Parser 204 and perform common conversions preemptively. This will improve the responsiveness of the system components, in particular, the Output Module 213 and the Web GUI 208; however, the trade-off is an increase in storage required, and also a slight decrease in the overall security level.

A Web GUI 208 provides, e.g., medical staff with remote access to DCDS 32 via a secured web browser connection (https) 202. Such a Web GUI 208 can provide an interface to perform administrative tasks such as setting up rules for Event System module 209, as well as an optimized interface for identifying images and sending output messages. The typical operations of these interfaces are described in detail below.

Web GUI 208 can operate on the structured metadata 206 to find and identify images. It can be configured to request conversions from Image Converter 211 to, e.g., display thumbnails and previews of images, and to provide service request forms where output messages can be specified and send on to Output Module 213 for delivery.

An adaptable Garbage Collector 207 can continually evaluate the state of all data and compare that to configurations made by an administrator of the system. The configuration can set certain criteria that items need to meet in order to remain in the system or be deleted from the system. One basic criterion can be the age of an item. For example, if an item has been stored over a week ago or certain number of days ago could be automatically deleted. Other automatic deletion criteria can be the number of times an item has been previously sent, system state information stored, and the value of any metadata. This feature is in part useful for keeping the resource usage down, and also to aid patient confidentiality by removing patent data that the system is no longer needed to maintain.

It should be noted that in some embodiments the images are to be used for clinical or diagnostic purposes. In such instances, it is often required that the image that is ultimately displayed on the device used for viewing the images maintain a certain resolution or image quality. As such, in certain embodiments, one or more of Parser 204, Event System module 209, and Image Converter 211 can be configured, either alone or in combination, to recognize that the image is being viewed in a diagnostic or clinical application. Such recognition can be based on information included in the meta data, information stored in Image System 214, or information provided via GUI 208.

For example, the address or device identified in the meta data for receiving the image can be recognizable as an address or device associated with a clinical or diagnostic application, the image or series identifier can also be associated with a clinical or diagnostic application, etc. Alternatively, an operator can indicate through GUI 208 that images to be sent are intended for clinical or diagnostic purposes.

When it is determined that the images are to be used for clinical or diagnostic purposes, then Image Converter 211 can be configured to determine, e.g., based on information stored in storage system 214, the required resolution or image quality. For example, resolution, image quality, or both for various types of images, clinical applications, etc., can be stored in storage system 214. Image converter can then determine the correct image resolution and quality and covert the image in accordance therewith. In certain embodiments, DCDS 32 can be configured to determine whether the identified output device or address is capable of displaying the converted image with the requisite image resolution and quality before sending the image. If the device or address is not capable, then DCDS can generate an error message or other notification indicating such. The error message can be displayed through GUI 208, on the device, or both.

Figure 3:
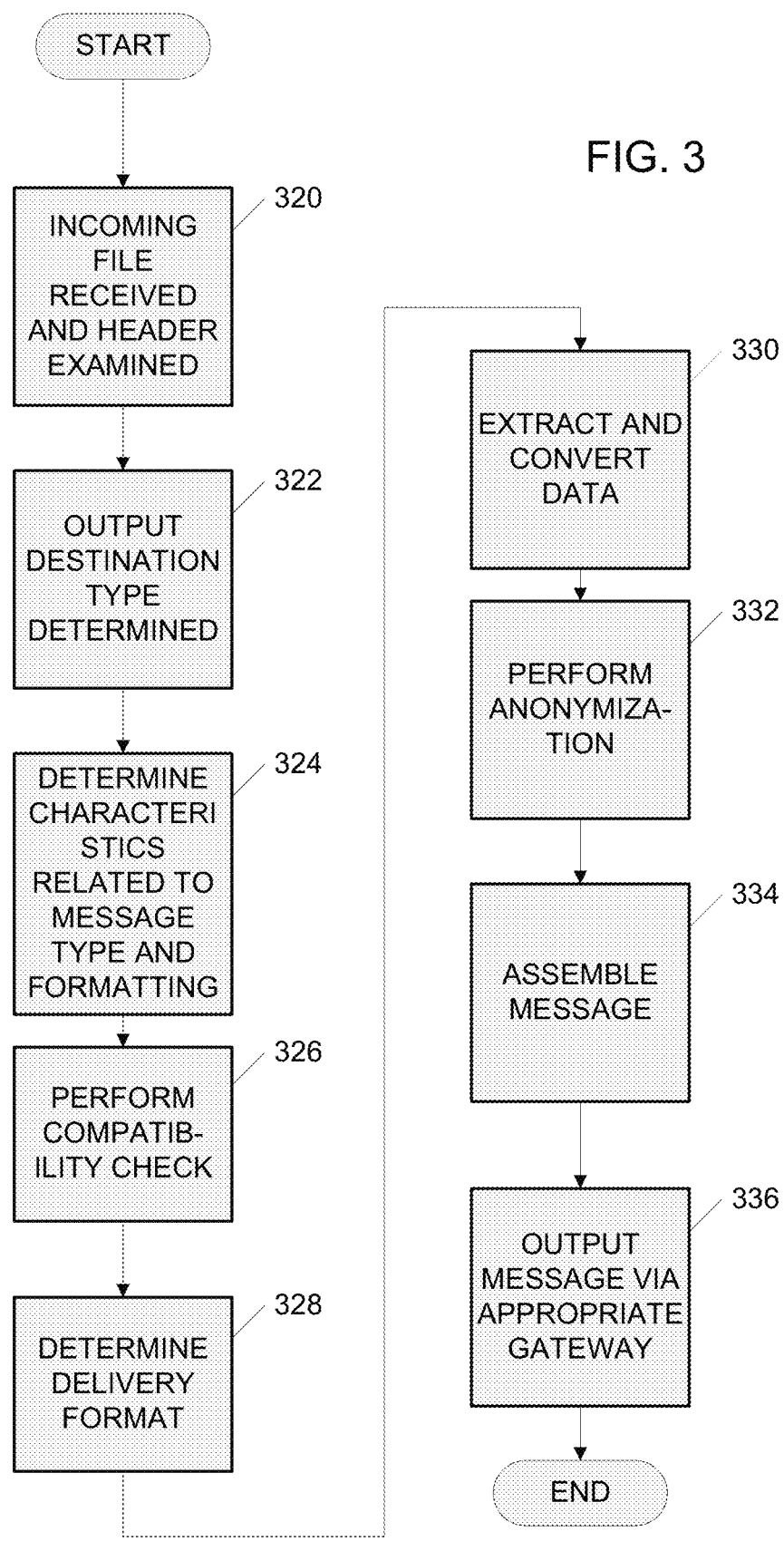
FIG. 3 is a flow chart illustrating an example automated message creation process performed by the data conversion and delivery system of FIG. 2 in accordance with one embodiment.

As noted above, DCDS 32 can be configured to take an incoming medical image file and automatically convert it for distribution to and viewing by any of a plurality of output modalities. FIG. 3 is a flow chart illustrating one example embodiment for an automated message creation operation performed by DCDS 32 in accordance with one embodiment. In the example of FIG. 3, it is assumed that destination information, e.g., output modality information is included in a medical image file received by DCDS 32. In other embodiments, a user can access DCDS 32, e.g., through GUI 208 and specify which files should be sent to which output modalities; however, a powerful aspect of DCDS 32, as configured in accordance with the systems and methods described herein, is its ability to automatically determine the destinations and to convert and format the data appropriately as described below.

In step 320, a file is received and the headers associated therewith are examined to determine various information. The medical image file received by input 203 will often include metadata that provides information related to the medical data or images included therewith. For example, in a DICOM file, the medical image file will include a header that comprises a plurality of fields. These fields are generally the same for each input modality 10. Thus, DCDS 32 can be configured to examine the header fields to determine various information as described in detail below and with respect to FIG. 4.

In step 322, an output destination type, or modality can be determined. For example, the header can include information identifying recipients of the images included in the image file. Or more specifically, the header can include information identifying output modalities associated with various recipients or services, e.g., such as an online photo album page, site, or service; a social networking page or service, a mobile device, etc. Basic types of destinations can include a mobile device, such as a cellphone; an email account; a Web-Application Specific Interface (API), e.g., associated with an online site or service, etc. Thus, DCDS 32 can be configured to examine the header file and determine associated output devices or services, i.e., modalities.

Whenever possible, DCDS 32 can be configured to then retrieve specific characteristics of each destination type as indicated in step 324. These characteristics can include capabilities and physical characteristics of the destination device and specifications and limitations of the network class and message type. This information is then used to determine the output formatting and other specifications needed for each output modality. For example, this information can be used for adaptations of the image data based on specifications for the type of message being sent, e.g., e-mail has limitations in specification and common practice that can be adapted for; and MMS has very different limitations that can be adapt for.

The capabilities and characteristics determined in step 324 can include frame size, i.e., pixel dimensions of an image or video, e.g., 640 by 480 and the like; data rate or data size, e.g., MMS messages can commonly not exceed 300 KB total size, e-mail attachments exceeding 10 MB are often not accepted, etc.; supported encoding format, e.g. mpeg 4, jpeg, etc.; and message layout rules, i.e., how a message can be composed for the destination, e.g. MMS is made of "pages", each able to display a single image or video and a single text along with playing audio while e-mail is capable of HTML layouts and can hold attachments of any file type, etc.

In step 326, a basic compatibility check can be performed to determine whether the data included in the image file can be delivered in a format compatible with the output modality. For example, if the image data includes video data, then a determination can be made as to whether the output modality is capable of receiving and displaying video data.

The most suitable delivery format is then chosen in step 328 to ensure the output message that is ultimately generated includes the best quality data that the output modality can handle. This can be important for example in clinical settings or settings where the data is being used for examination or diagnostic purposes. Resolution information suitable for diagnostic purposes and the ability of DCDS 32 to provide such resolution is discussed in detail below.

Then, in step 330 the data can be extracted and converted as required. For example, MMS messages allow only a very limited total message size. Therefore images or video in particular often need to be adapted and optimized to let the final message meet the format and specification requirements of a particular output modality. In contrast, e-mail messages often have no strict limit on size and therefore can accept larger files, e.g., higher resolution images or video. But even e-mail accounts can include rules limiting extremely large files and therefore even e-mail messages can require optimization of, e.g., video files to ensure sufficient quality but also to comply with size limitations.

If the incoming file is already encoded in a format compatible with the output modality, then often no conversion will occur in step 330 in order to preserve the highest possible image quality.

In step 332, the data can be anonymized as required by any applicable anonymization rules. For example, the data can be extracted and copied into a generic format so that certain data can be removed, redacted, etc. The data can then be converted to the final output format. Steps 330 and 332 can be performed in parallel or reverse order as required by a particular implementation.

In step 334, the converted data can then be assembled into an output message in accordance with the applicable formats and specifications determined in the preceding steps. Optionally, other data can be included with the message. This information can be manually entered, e.g., via GUI 208 or it can be extracted from the metadata accompanying the received file. Still further, the data can be data retrieved from configuration settings based on the set of characteristics described above.

In certain embodiments, the data components that are to comprise an output message are assembled according to template rules for the type of message being created. For example, the various template rules can be stored in Storage System 214 and accessed by Output Module 213 in order to assemble the output message. For example, MMS messages are based on a page metaphor where each page can contain an image or video, a text element, and an audio element. Thus, sending two or more images, or including text, audio, or both with the image(s) will then require the message to be assembled into several pages. By contrast, e-mail messages can include any number of images, attachments, etc., depending on, e.g., the message size restrictions.

Output Module 213 can then be configured to elect the appropriate output gateway for transmission of the assembled output message in step 336. For example, Output Module 213 can be configured to send an e-mail message to a SMTP server (not shown) and to send an MMS message to a MMS gateway (not shown).

Figure 4:
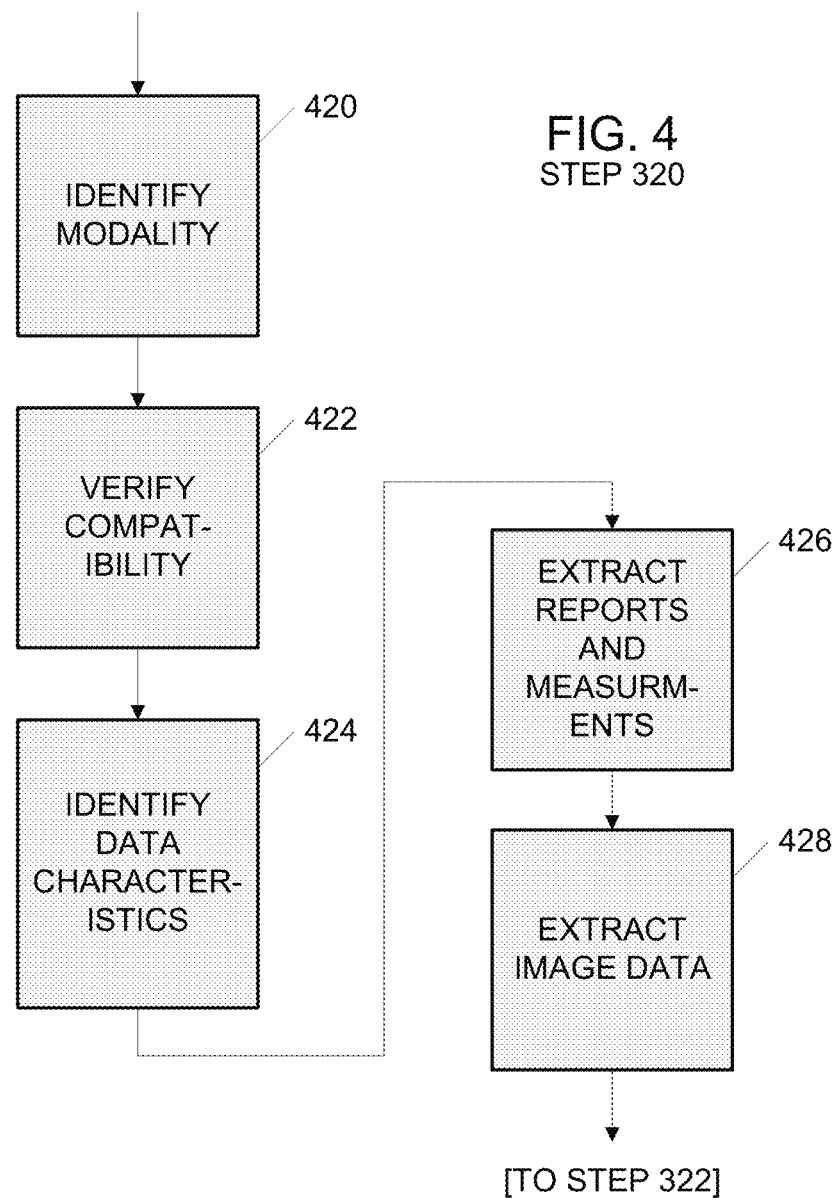
FIG. 4 is a flow chart illustrating example type of information and data that can be examined in the process of FIG. 3 in accordance with one embodiment.

FIG. 4 is a flow chart illustrating example type of information and data that can be examined in step 320. As can be seen in FIG. 4, when the file comes in, the metadata or more specifically the header can be examined to identify the input modality in step 420. In step 422, the compatibility of the modality determined in step 420 with the system can be determined. If compatible, then in step 424, specific characteristics of the data included in the image file can be determined. For example, whether or not the file actually includes any image or video data or whether the data is simply report or measurement can be determined in step 424. When an incoming file does include, e.g., report or measurement data, then such information can be extracted and stored in, e.g., a generic structured format in step 426. In step 428, any image data can then be extracted and stored as well and various characteristics can be determined such as binary encoding format, frame size, color bit depth, still image or video, etc.

Figure 5:
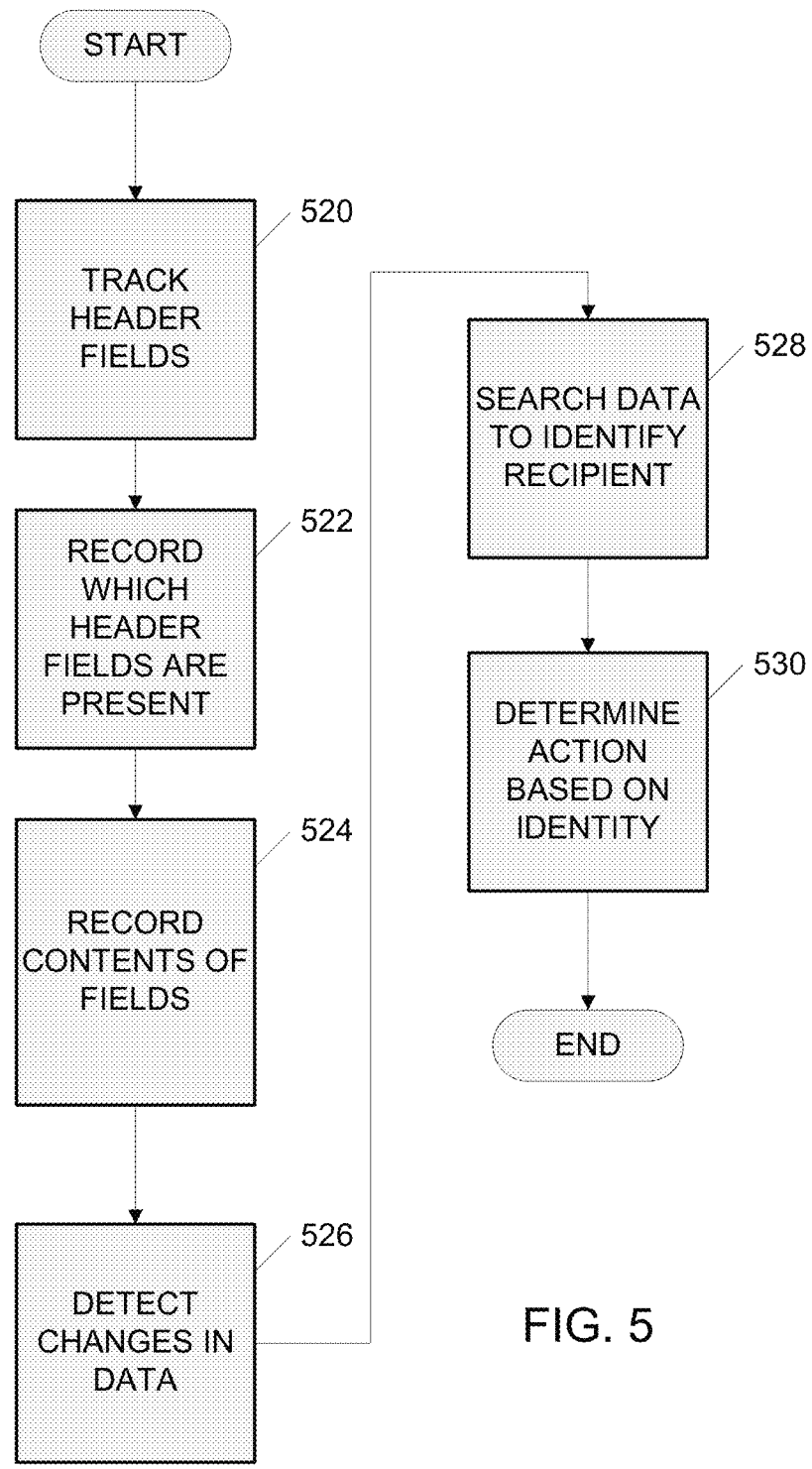
FIG. 5 is a flow chart illustrating an example process for the use of information embedded inside of the metadata included with incoming files by the data conversion and delivery system of FIG. 2 in accordance with one embodiment.

FIG. 5 is a flow chart illustrating an example process for the use of information embedded inside of the metadata including with incoming files by DCDS 32 in accordance with one embodiment. The metadata, e.g., header fields can be used to ensure safe and secure delivery of the image data included therewith. For example, a DICOM image file can include a plurality of header fields that are key-value pairs in a number of datatypes, such as strings, numbers, dates, special measurement types, etc. Fields can be embedded in the and can be hard linked to the file for which the provide metadata. In this way, there is no way to mix-up header files and the associated data, since they are not separated.

In step 520, DCDS 32 can be configured to automatically track and record header fields for each network device sending images. In this way, DCDS 32 can identify the specific device associated with an incoming file. DCDS 32 can do this by recording which header fields are present for a particular modality 10 in step 522 and to then record the data included in device-dependent header fields for the associated modality in step 524. A particular device should always report the same values for, e.g., manufacturer, model name, model number, etc. Thus, DCDS 32 can use this information to identify a particular device.

In step 526, DCDS can detect any changes in the data and then take appropriate action. For example, changes to header field data that should not be changed, e.g., manufacturer information, can be an indication that the file has been tampered with or someone is trying to hack into the system. In response to detection of such changes, the system can log the event, notify an operator, place the incoming data in an approval queue, quarantine the data or any further data from the associated device, reject the data, rejecting the all future data from the device, to name just a few possible actions.

In step 528, DCDS can be configured to search the header fields for data that can identify an intended recipient as noted above. Identification can be in the form of an actual, e.g., e-mail address, mobile station International Subscriber Directory Number (ISDN), web site address, etc. In fact, such direct identification can be preferable as it takes advantage of the existence of the header fields. Identification can also be indirect such as an ID that can be used to look up a direct address, e.g., in a registry stored in storage system 214. It should also be noted that each field can include more than one piece of data and data of different types. Accordingly, any identifying or address fields can include telephone numbers as well as e-mail address, etc. Further, identifying data can be included in more than one field.

The DCDS 32 can be configured to then determine an action to take in step 528 based on any identifying data detected in step 530. Such actions can include sending an appropriate message to any addresses found, formatting messages appropriately as described above, notifying an operator, adding a message to a queue, e.g., for manual approval, locating and adding other data or information to an outgoing message, to name just a few.

Figure 6:
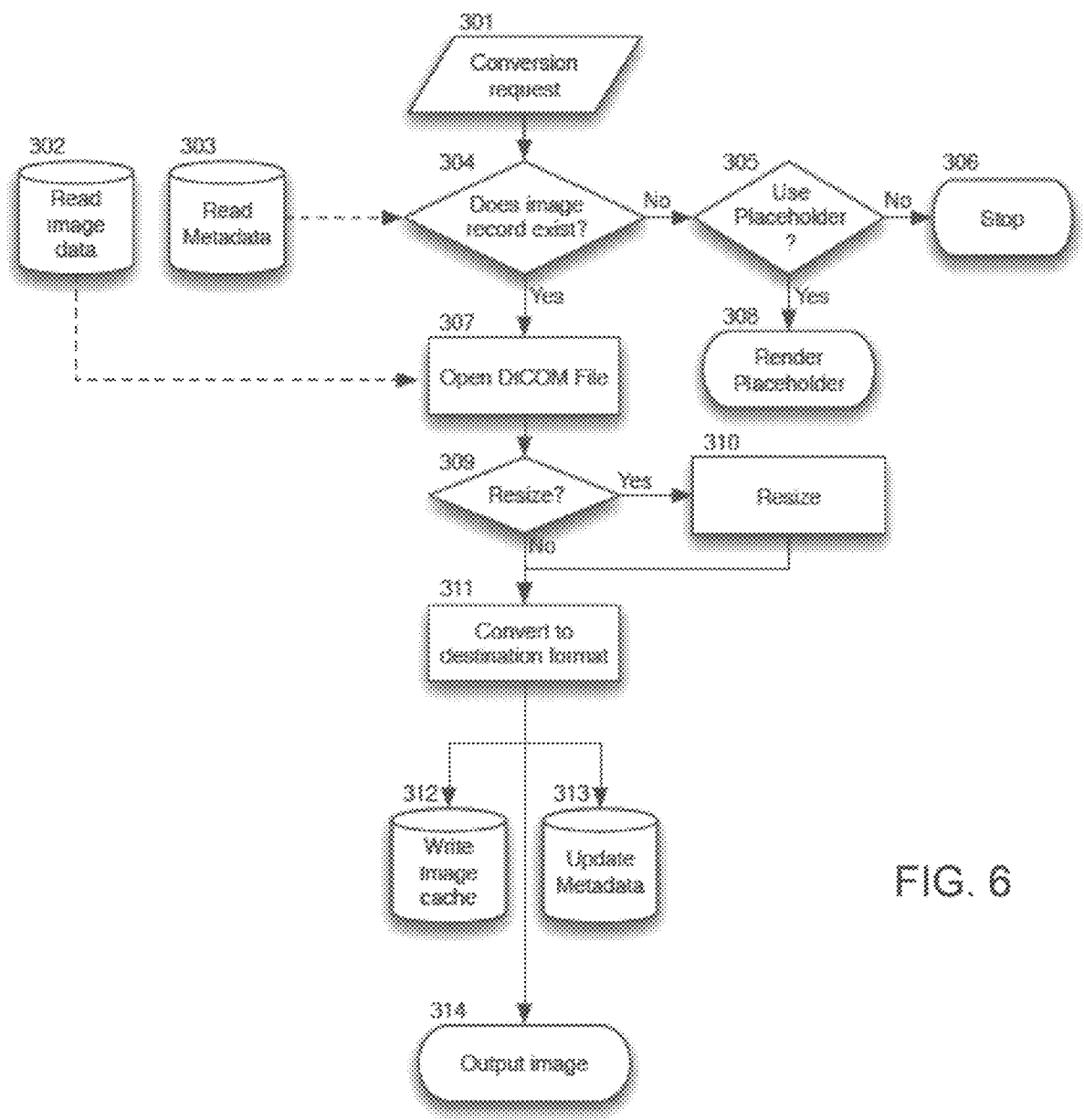
FIG. 6 is a flow chart that illustrates the operation of an image converter module that can be included in the data conversion and delivery system of FIG. 2.

Accordingly, FIG. 6 is a flow chart that illustrates the operation of DCDS 32 in more detail. Referring to FIG. 6, a Conversion Request 301 can be received containing, at a minimum, an internal identifier for the image, and a destination format. As noted above, the conversion request can be the result of information and data included in the metadata associated with an incoming file. As noted below, however, the request can also result from input received through GUI 208. Optionally, the request could contain new image dimensions to be scaled as output image to be sent. The Image Converter 211 can be configured to then determine the existence of the requested image 304 by trying to locate the metadata associated with it in metadata database 303. If no record exists for the requested image, the converter can optionally return a placeholder image (305, 308) or abort the conversion attempt 306. A placeholder is typically an image, video or similar media communicating that the requested image is unavailable. At this point, the converter also can also be configured to determine if the requested output format is feasible or not.

If a metadata record in database 303 does exist, then the converter can be configured to load the, e.g., DICOM image 307 from image storage 302 into a raw binary format. The Converter 211 can be configured to then determine if the image data should be resized to the dimensions provided in the request or to the dimensions required by the requested output format. For example a jpeg preview for the Web GUI 208 could be rendered in any dimensions that are suitable to the layout of the html document, while video for MMS messages have very specific dimensions to comply with the specification.

Next, the image data can be converted 311 to the requested destination format. The results can be saved to an image cache 312 and metadata records can be updated 313 to indicate the existence of the converted image. Finally, the converted images can be returned as a response to the request. Converter 211 can then return either the converted binary data directly or return a reference to its location in the image cache 313.

As noted, DCDS 32 can also be operated and interfaced with through the Web GUI 208. GUI 208 can enable both remote and local access the DCDS 32 and allows for images to be located within storage system 208. The images may need to be located or analysis or diagnosis or for sending to a specified destination or address.

Two primary ways for accessing files can be provided. The first way involves finding files without any identifying information. This is explained in detail with respect to FIG. 7; however, it should first be noted that each device sending files to DCDS 32 can be identified by recording and mapping header fields of incoming file transfers. The devices can also be at least partially identified based on their network address, AE titles used for the transfer, or both. Each device can then be given a name that is unique and preferable meaningful to operators. Files as well as their series, study, or both, can then be identified by the device they originated from, the time and date of the image capture, and header fields identifying the operator of the device used to capture the images.

Since no patient information is needed, DCDS 32 can handle anonymized data and no patient information can be gathered by the misuse of the system. Further, the most used images can be stored as the most recent images in the system. Thus, finding images can be made very efficient in this manner. Once the file, series, study, etc., had been found, GUI 208 can offer the operator direct access to features for viewing the images, sending the images, etc.

Figure 7:
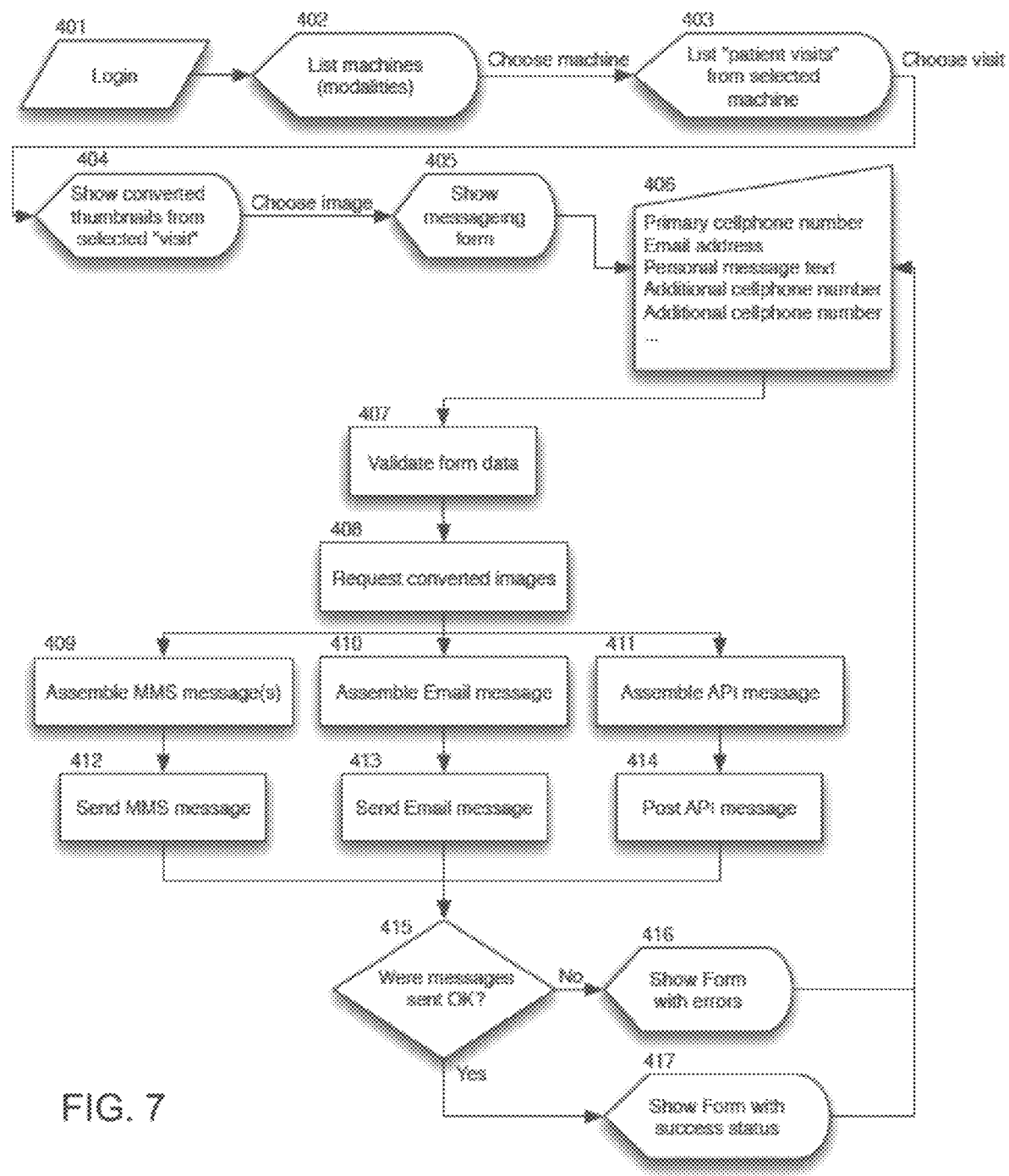
FIG. 7 is a flow chart illustrating a typical use of a Web GUI that can be included in the data conversion and delivery system of FIG. 2 and its streamlined interface for finding an image by the originating modality without any identifiable patient information in accordance with one embodiment.

With this in mind, FIG. 7 is a flow chart illustrating a typical use of the Web GUI 208 and its streamlined interface for finding an image by the originating modality without any identifiable patient information (401-404) in accordance with one embodiment. When an image has been identified (405) the interface displays a service request form where the user enters output destination information and other message details. If the data validates (407) the required conversions are requested (408) from the Image Converter (211.) For all successful requests, the data is assembled by the appropriate output plug-ins (409-411) and the results are sent (412-414) to the appropriate destinations. Status information for each individual output is gathered (415) and returned (416 or 417) to the form view (405) for display. At this point, the user can choose to repeat the send process or return to finding another image.

The Web GUI 208 allows for sending groups of images that belong to the same, e.g., DICOM Series. The operating steps are similar to those illustrated by FIGS. 7 and 8. The Web GUI 208 also present interfaces for configuring the Event System 209, organizing and storing output destination addresses and other administrative tasks necessary. It is important to note that, as a security measure, the Web GUI 208 does not handle any authorization of source modalities allowed to store images or access privileges to those images. These important settings are only available through a separate method of access either locally or remotely. With the DCDS running on a Unix-style operating system, remote access would typically be via the Secure Shell (SSH) protocol. If the DCDS is running on a Windows operating system, remote access would typically be via Terminal Services. Both protocols are examples of secured remote access to the operating system.

The second way to access files is to use identifying information. For example, operators can search for files using patient information such as name, birth date, patient ID, etc. The operator can, for example, input a search term and if there is a match, the system can present all available studies. If multiple patients are returned, then they can be presented for selection. Once the patient is selected, and the associated file, series, study, etc., had been found, GUI 208 can offer the operator direct access to features for viewing the images, sending the images, etc.

Figure 8:
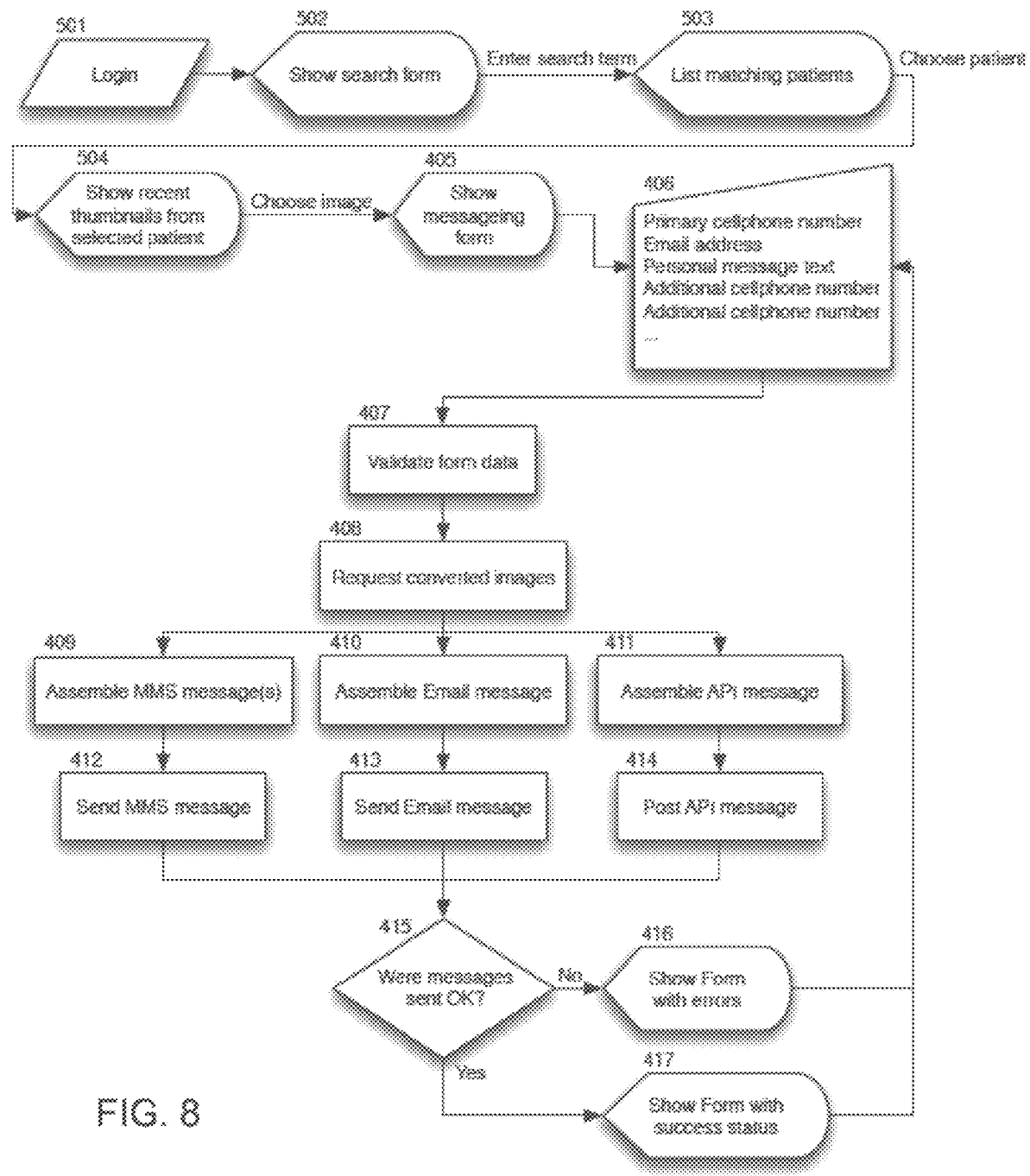
FIG. 8 is a flow chart illustrating a variation of the typical use of the Web GUI and its streamlined interface for finding an image by using a piece of identifiable patient data in accordance with one embodiment.

FIG. 8 is a flow chart illustrating a variation of the typical use of the Web GUI 208 and its streamlined interface for finding an image by using a piece of identifiable patient data (501-504) such as, patient name, and birth-date, etc. Alternatively, any unrelated identifying password or PIN code can be utilized to avoid using real patient information to ensure patient privacy. After that, the processing steps as described above related to FIG. 7 can be followed.

Figure 9:
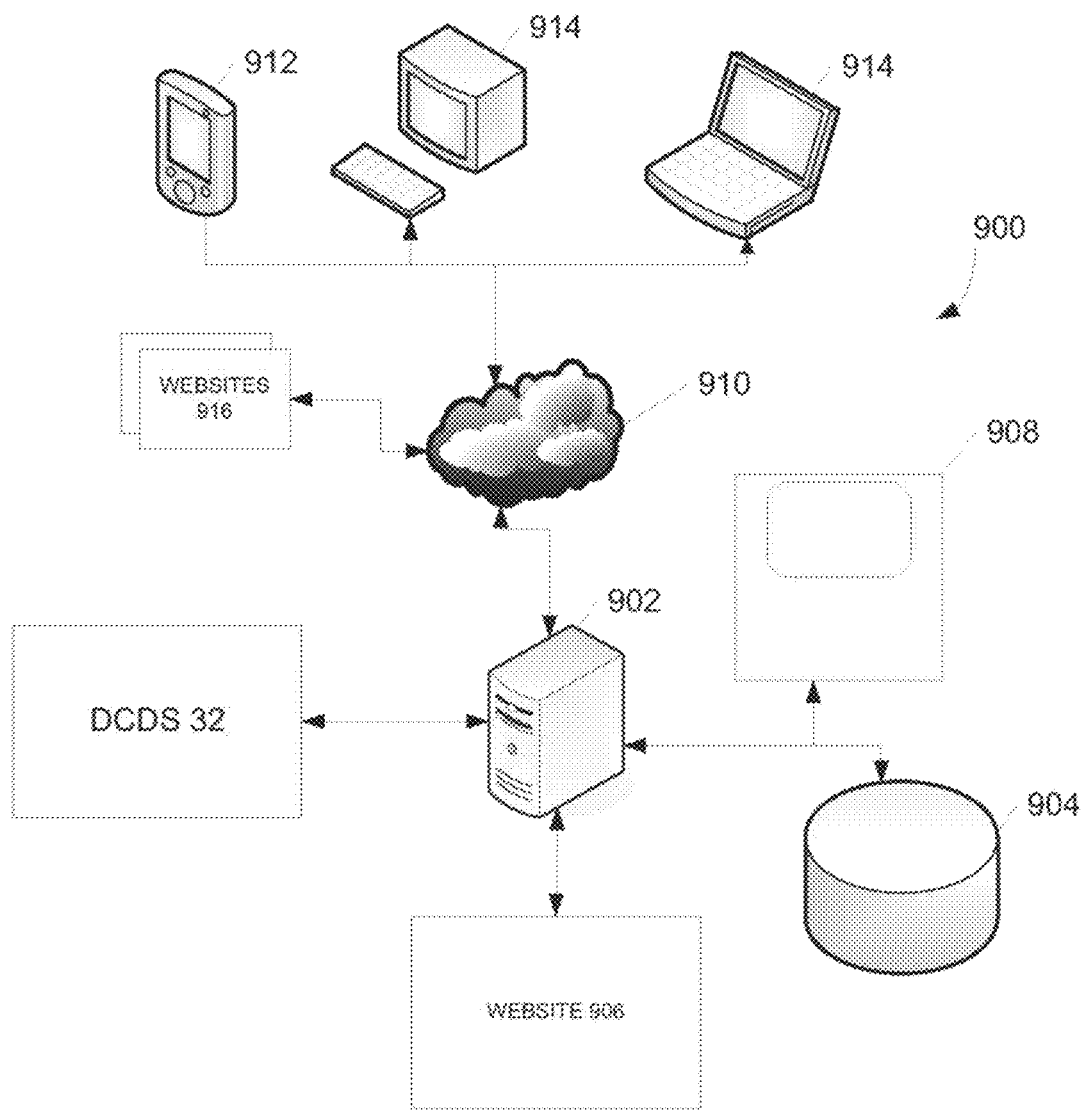
FIG. 9 is a diagram illustrating an example system for the automatic conversion and distribution of medical images to any of a plurality of output modalities in accordance with another embodiment.

In certain embodiments, CCS 30 can be interfaced with a server 902 that can be configured to host and support various value added services for, e.g., patients and family in relation to the images being captured by modalities 10 as illustrated in FIG. 9. For example, if the images are fetal ultrasound images, the server 902 can be configured to provide a variety of services for the parents, family, friends, etc. For example, the DCDS 32 can be configured to convert the images to a proper format or formats supported by server 902 and the related services. The images can be sent to server 902 and stored in storage system 904.

It will be understood that server 902 can actually comprise a plurality of servers, computers, routers, etc., as well as the appropriate software and firmware required to carry out the functions described herein. Further, storage system 904 can comprise one or more databases, one or more storage servers, as well as other physical storage mediums as required.

Server 902 can then be configured for example, to host a web site on which users can create accounts. The users can then access the images on the site and purchase images, pregnancy calendars, customized mugs, key chains, T-shirts, canvases, etc. Further, the site can be configure to present pictures, illustrations, information on fetus and child development, health and nutrition tips, etc. Such a site can enable such services as a registry, e.g., for a baby shower; automatic updates to friends and family; digital and viral gifts, such as baby images with digital lullabies; invites and thank you cards; etc.

A user can be charged a fee for setting up an account, e.g., a subscription fee, either one time or periodic, the user and family and friends can also be charged for the various products and services, or both.

In addition, kiosks 908 can be set up, e.g., in maternity wards that can provide at least some of the same services. Kiosk 908 can either be stand alone, i.e., interfaced directly with CCS 30, or can be interfaced with server 902 as illustrated. Thus, family and friends can order pictures and other goods, e.g., right in the waiting room.

Further, the user can continue to use the account even after the birth of the child. For example, the site can track the child throughout its child hood, or at least through the first few months or years. The site can be configured to send birthday reminders and announcements to friends and family or to inform of other special events, developmental milestones, etc. Moreover, the site can be configured to continue to present developmental information as well as health and nutrition tips for both mother and child.

In fact, it can be preferable to have the parent upload contact information for friends and family. In this manner, server 902 can be configured to continue to send birthday reminders to friends and family. In certain embodiments, the site hosted by server 902 can be affiliated with or host a "gift store" offering various products and services. Alternatively, or in addition, the site can offer discounts, coupons, etc., to various other business and stores. Since server 902 will have pertinent demographic information related to the child, e.g., residence information, sex, age, race, and possibly even parents age, profession, and other affiliations, the site can send reminders, gift recommendations, discount offers, etc., that are appropriate for the child and the family, popular with similar demographics, etc.

In this regard, it can be preferable to offer the user the opportunity to provide such demographic information. Thus, in one embodiment, the user can access the site and customize or provide profile information, contacts, preferences, etc. Algorithms running on server 902 can be configured to then use the information available to make product recommendations, etc. In fact, since server 902 will have information for individuals all over the world, the algorithms can be configured to use information for populations that share similar demographics, income levels, preferences, etc., to make recommendations.

In certain embodiments, a user can purchase items through the site, i.e., through server 902. For example, server 902 can be configured to accept credit card payment, a PayPal account, or for mobile billing. Thus, server 902 can be configured to process the transaction and either deduct an appropriate fee or charge a related business, affiliate, partner, etc., a transaction fee. Moreover, purchase information can also be fed into the algorithms and used to make future recommendations. In fact, the purchases of an entire related population can be used to make more targeted and appropriate recommendations.

Thus, as a child grows, the algorithms can be constantly updated and honed in order to make, e.g., gift recommendations. Recommendations that can be automatically sent out to friends and family over the years. As the database grows over time and with more and more users, the algorithms can be honed to provide ever more relevant and targeted recommendations.

It should also be noted that the database will necessarily include vast information about the relationships and connections between a large population. This includes direct links such as friends and family, but also more indirect links such as preferences, similar buying habits, etc. This type of interconnection information can be very valuable for targeted advertising and product recommendations as well as for simply tracking and mapping the interconnectedness of a large population.

It should be pointed out that such a site can be built around other conditions or events, such as a cancer support site, physical therapy support site, etc. It should also be pointed out that the merging of interconnectedness data for these various other conditions and events can extend the power of the information and lead to even better algorithms for targeting information and products and services.

It should also be noted that users can access the site via, e.g., the Internet using computers 914 and mobile devices 912. Further, the site can be interfaced with other social networking sites such as Twitter, Facebook, etc. In certain embodiments, the site can actually be converted to an application, or widget that can be exported to other sites. For example, a grandma can place the application on her Facebook page and receive updates and notices more easily without needing to log onto server 902. This can increase the interaction with the site, which can increase, for example, the amount of information and data available to server 902 as input to the algorithms described above.

While certain embodiments have been described above, it will be understood that the embodiments described are by way of example only. Accordingly, the systems and methods described herein should not be limited based on the described embodiments. Rather, the systems and methods described herein should only be limited in light of the claims that follow when taken in conjunction with the above description and accompanying drawings.

Peripheral Encryption and Conversion Device

Figure 10:
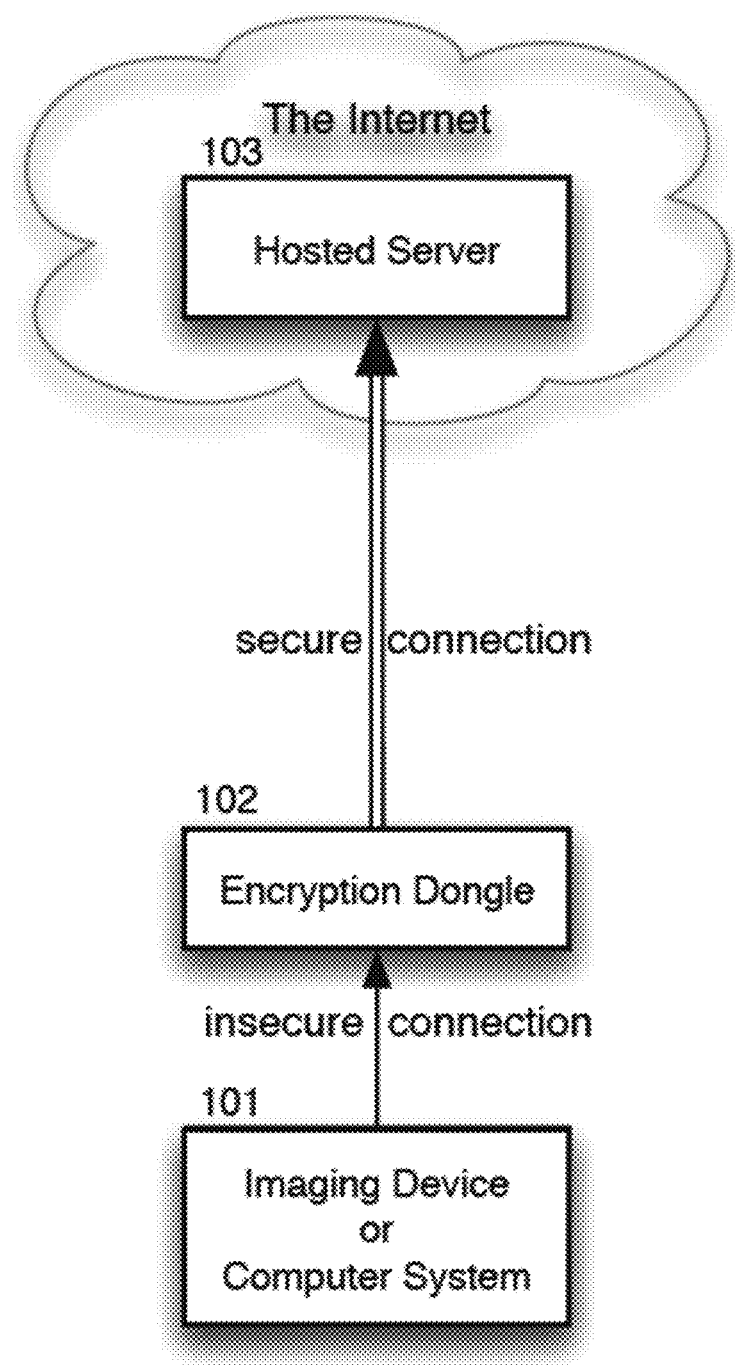
FIG. 10 is an illustration of a peripheral device connected with a medical imaging device and a remote server for converting and encrypting medical image files from the medical imaging device, according to one embodiment of the invention.

In one embodiment, a peripheral device may be attached with a medical imaging device for the encryption and conversion of a medical image into a secure and standardized image file format as well as the communication of the encrypted and/or converted image to a secure server on a remote network. As shown in FIG. 10, the peripheral device 102 may be a dongle or other type of stand alone device which can be physically attached with a medical imaging device 101, and will have its own processor and memory for executing a variety of functions relating to the conversion, encryption and transmission of medical image files from the medical imaging device to a remote server 103 on another network. The peripheral device 102 may be attached with a communication port on the medical imaging device, such as a network port, serial port or other communication interface. The peripheral device may act as a filter to monitor all medical image files generated on the medical imaging device and encrypt and convert selected medical image files for transmission to a remotely connected device on another network, such as a server or a mobile device.

The dongle may be configured with a separate network connection to a local area network (LAN) or wide area network (WAN), or it may be configured to use the network that is already connected with the medical imaging device. If the medical imaging device is not connected to a network or is connected to a network that is not capable of transmitting medical images, the dongle may have network hardware to allow the dongle to communicate over a WiFi or cellular network or even accept a direct Ethernet cable connection to a local network which the medical imaging device is not connected with.

In another embodiment, the encryption dongle 102 may be connected with the imaging device 101 with an insecure connection, in which case the encryption dongle 102 will function to take medical images stored on the medical imaging device 101 and encrypt the images for transmission across a secure network connection to a remote device, such as a remote secure server or a mobile device that is the ultimate destination of the medical image.

One embodiment provides a method and technical system for encrypting and routing DICOM network connections from devices without any such encryption capabilities built-in.

One embodiment of the invention can listen on known ports for unprotected communication and automatically encrypt and route the connection in its encrypted form over the port's encrypted counterpart. E.g. ordinary DICOM connections on TCP port 104 or 11112 can be encrypted in SSL/TLS and routed as DICOM/TLS on TCP port 2762. This would effectively make the connection appear to the remote server as a secure TLS connection and to the client device as an unprotected connection. By attaching the embodiment of the invention to the network port of an imaging device or as a network router on the same protected local network as the device, a high level of security is maintained.

Likewise, ordinary "web" connections over the HTTP protocol on TCP port 80 can be encrypted in SSL/TLS and routed as HTTPS on TCP port 443. This would effectively make the connection appear to the HTTP server as a secure HTTPS connection and to the HTTP client as an unprotected connection. It should be noted here that encrypting HTTP traffic is useful only with older clients and servers which are capable of secure connections. It is, however, a well-known pair of network ports that serve to illustrate a general embodiment of the invention.

Embodiments of the invention include a wireless network connection such as WiFi or cellular modem capabilities to not only encrypt but also to offer access to the Internet without existing network infrastructure near the imaging device. This is highly useful for portable devices that can be used on-the-go running on battery power.

Embodiments of the invention can be pre-configured to only forward protected traffic to a single remote end-point.

Embodiments of the invention may use any and all relevant encryption methods to secure the connection. Examples or these include the aforementioned SSL/TLS standard as well as other common encryption standards. The point being that the invention will mimic the native encryption standard for each type of connection an embodiment supports. Encryption may be encoded and decoded either by dedicated chips (electronic hardware components), software or a combination of software with hardware acceleration.

Network Encryption and Conversion Device

A network device for connection with a local network including at least one medical imaging device provides for the encryption and conversion of a medical image from the at least one medical imaging device into a secure and standardized image file format, as well as the communication of the encrypted and/or converted image to a secure server on a remote network. The network device may act as a router or a gateway on the local network to monitor traffic of medical images from the medical imaging devices to destination devices outside of the local network and ensure that the medical data files are encrypted and converted into an appropriate format for delivery to a device on the remote network. Upon detection, the network device will encrypt and convert the selected medical image files for transmission to a remotely connected device on the remote network, such as a server or a mobile device.

Figure 11:
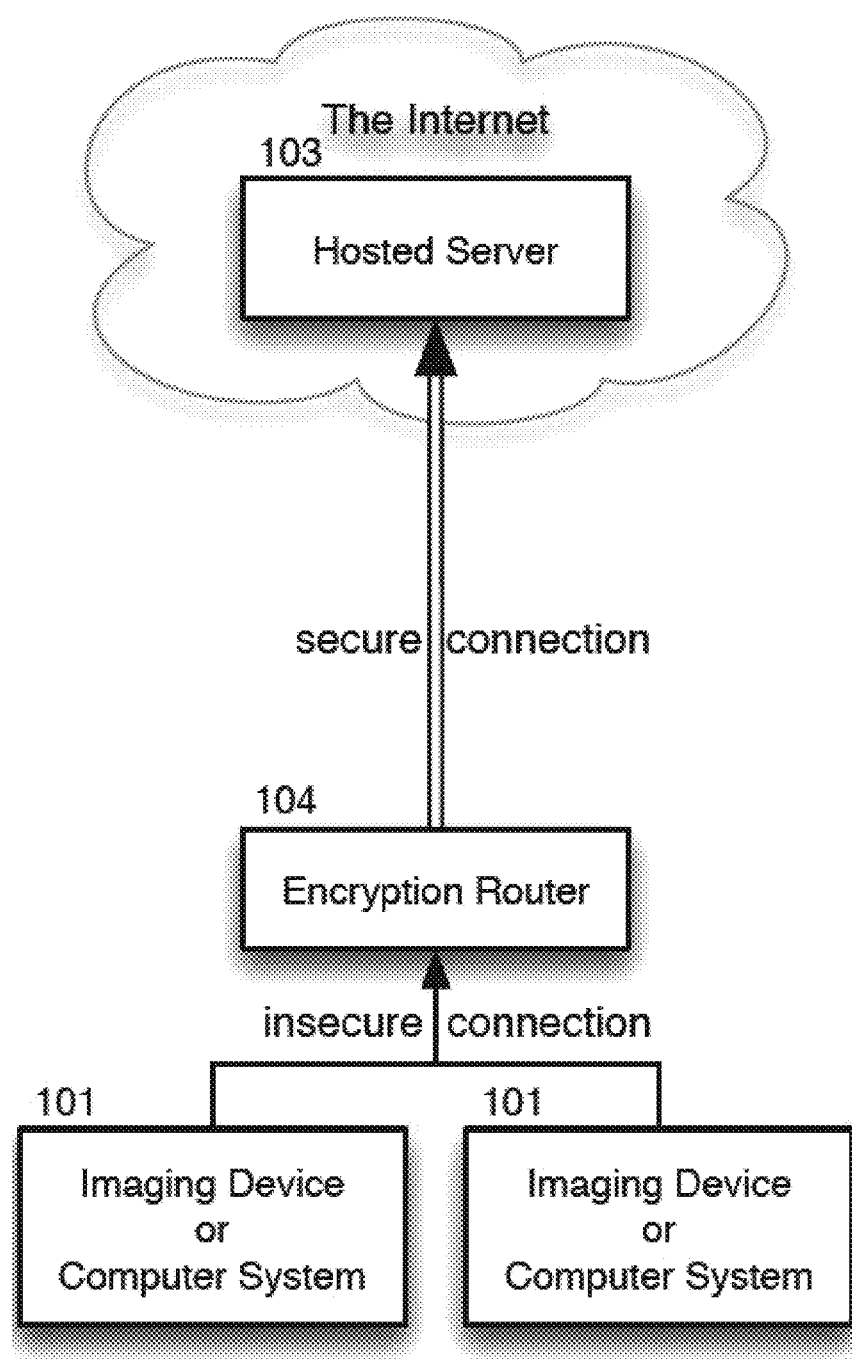
FIG. 11 is an illustration of a network device connected with a medical imaging device and a remote server for converting and encrypting medical image files from the medical imaging device, according to one embodiment of the invention.

One embodiment of the network device is illustrated in FIG. 11, where the network device 104 acts as an encryption router to receive medical image files from one or more medical imaging devices 101 over a local network which may not be secure. The encryption router 104 will then be configured for encryption and conversion of a medical image into a secure and standardized image file format. The encryption router 104 will then be configured for communication of the encrypted and/or converted image over a secure connection to a secure server 103 on a remote network, such as the Internet.

In one embodiment, the network device 104 will create a private network for the one or more medical imaging devices 101 to communicate. The network device 104 may then transmit an encrypted DICOM image over WiFi, cellular (3G) or cable connection to a remote network. In this configuration, the network device 104 acts as the network gate to ensure that all medical images being transmitted out of the local network are converted and encrypted.

Figure 12:
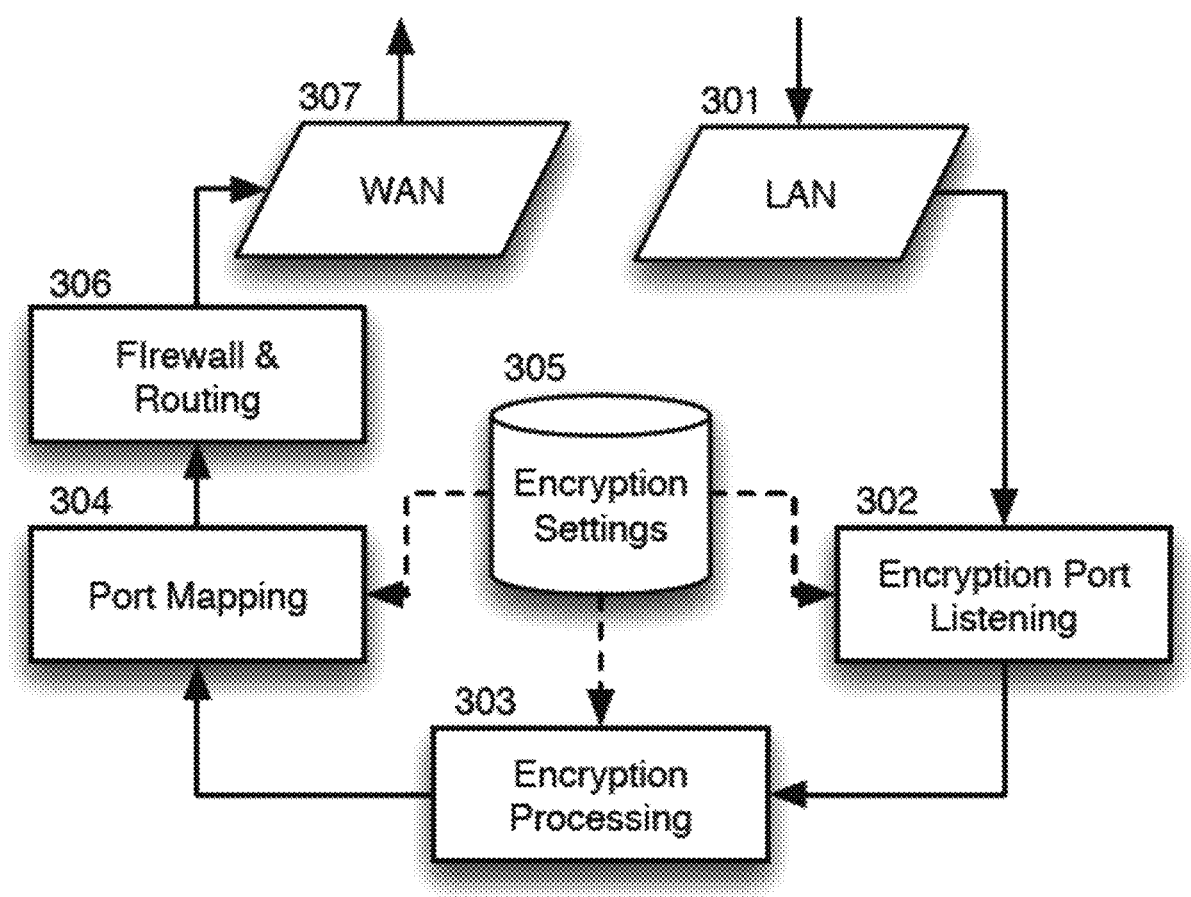
FIG. 12 is a flowchart diagram of the signal flow through the network.

FIG. 12 illustrates a flowchart of the data flow of a medical image file from a local area network (LAN) 301 to a remote device on a remote wide area network (WAN) 307. The network device 104 may include one or more of the components illustrated herein, including an encryption listening port 302 which monitors network traffic in the LAN for the transmission of medical image files which are not encrypted or converted into a proper format. An encryption database 305 may store encryption settings that provide instructions on the type of encryption that a particular medical image file should be encrypted with, perhaps depending on the type of network or the destination device on the remote WAN network 307. The medical image file is processed 303 to encrypt the file, after which a port is mapped 304 for transmission of the file. The encrypted file is then transmitted through a firewall or other local router 306 to a remote WAN network 307.

In one example, a Vscan imaging device captures a medical image that is non-DICOM and not encrypted, but which is selected for transmission from the Vscan to a remote secure server on the remote network. The medical image is then sent to the network device 104, which converts the image to a DICOM image and encrypts the image before sending it to the remote secure server.

The network device may be useful in a local network which is otherwise insecure or unreliable, as it creates a secure connection with the medical imaging devices and with a remotely connected server or device on another network. Additionally, the network device may be useful in highly secure networks with strict firewalls that would otherwise prevent connections to a remote secure server.

In one embodiment, the network device may be configured as a network satellite which is attached with the local network but which acts as a remote secure server to that the one or more medical imaging devices sends the images to the network satellite under the impression that the network satellite is the final destination for the medical image file. The network satellite will then take the medical image and encrypt or convert it (or both) and then send the encrypted and converted image to the actual remote secure server. In this embodiment, the medical imaging device does not need to be instructed to send the medical image file to a new location on the network such as the network device, as it instead transmits the file to what it believes is the final destination of the medical file—the remote secure server on a remote network.

One embodiment provides a method and technical system for encrypting and routing DICOM network connections from devices without any such encryption capabilities built-in.

One embodiment of the invention can listen on known ports for unprotected communication and automatically encrypt and route the connection in its encrypted form over the port's encrypted counterpart; e.g., ordinary DICOM connections on TCP port 104 or 11112 can be encrypted in SSL/TLS and routed as DICOM/TLS on TCP port 2762. This would encrypt the data over a secure connection, while effectively making the connection appear to the remote server as a secure TLS connection and to the client device as an unprotected connection. By connecting this embodiment of the invention to the network port of an imaging device or as a network router on the same protected local network as the device, a high level of security is maintained.

Likewise, ordinary "web" connections over the HTTP protocol on TCP port 80 can be encrypted in SSL/TLS and routed as HTTPS on TCP port 443. This would effectively make the connection appear to the HTTP server as a secure HTTPS connection and to the HTTP client as an unprotected connection. It should be noted here that encrypting HTTP traffic is useful only with older clients and servers which are capable of secure connections. It is, however, a well-known pair of network ports that serve to illustrate a general embodiment of the invention.

Embodiments of the invention include a wireless network connection such as WiFi or cellular modem capabilities to not only encrypt but also to offer access to the Internet without existing network infrastructure near the imaging device. This is highly useful for portable devices that can be used on-the-go running on battery power.

Embodiments of the invention can be pre-configured to only forward protected traffic to a single remote end-point.

Embodiments of the invention may use any and all relevant encryption methods to secure the connection. Examples or these include the aforementioned SSL/TLS standard as well as other common encryption standards. The point being that the invention will mimic the native encryption standard for each type of connection protocol an embodiment supports. Encryption may be encoded and decoded either by dedicated chips (electronic hardware components), software or a combination of software with hardware acceleration.

Encryption and Conversion Plugin

Systems and methods for encrypting and converting medical image files on a device within a network are provided. An encryption and conversion unit may be incorporated within the hardware and software of a medical imaging device or another network device in order to provide the capability for encrypting a medical image for transmission to a remote network and for converting the medical image to a format that is compatible with a destination device or network. The encryption and conversion unit may also be configured to package and transmit a converted and encrypted image to an appropriate destination, such as a secure server, on a remote network.

The encryption and conversion unit may act as a router or a gateway on the local network to monitor traffic of medical images from the medical imaging devices to destination devices outside of the local network and ensure that the medical data files are encrypted and converted into an appropriate format for delivery to a device on the remote network. Upon detection, the encryption and conversion unit will encrypt and convert the selected medical image files for transmission to a remotely connected device on the remote network, such as a server or a mobile device.

Figure 13:
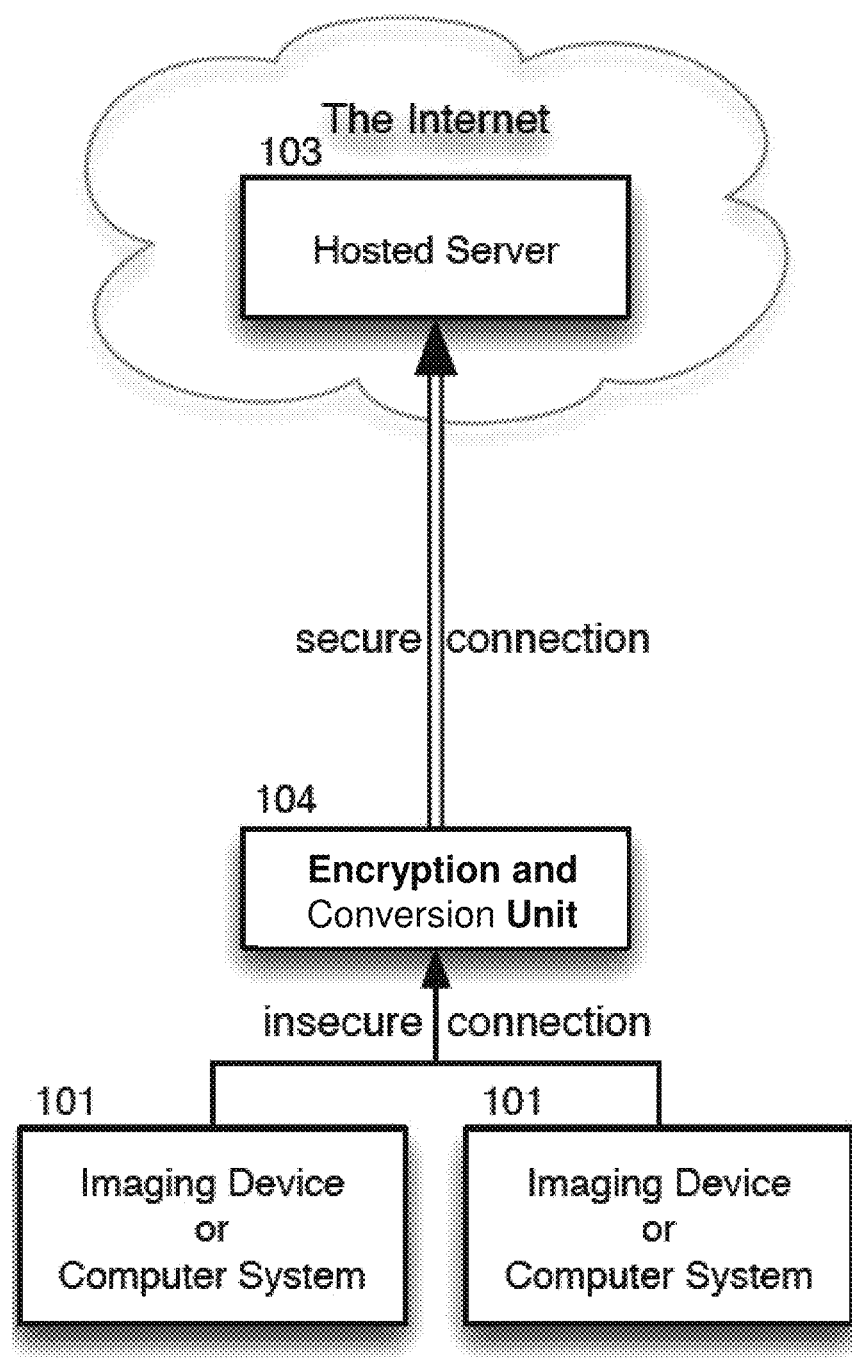
FIG. 13 is an illustration of a system for converting and encrypting a medical image with an encryption and conversion unit, a medical imaging device and a remote server, according to one embodiment of the invention.
Figure 14:
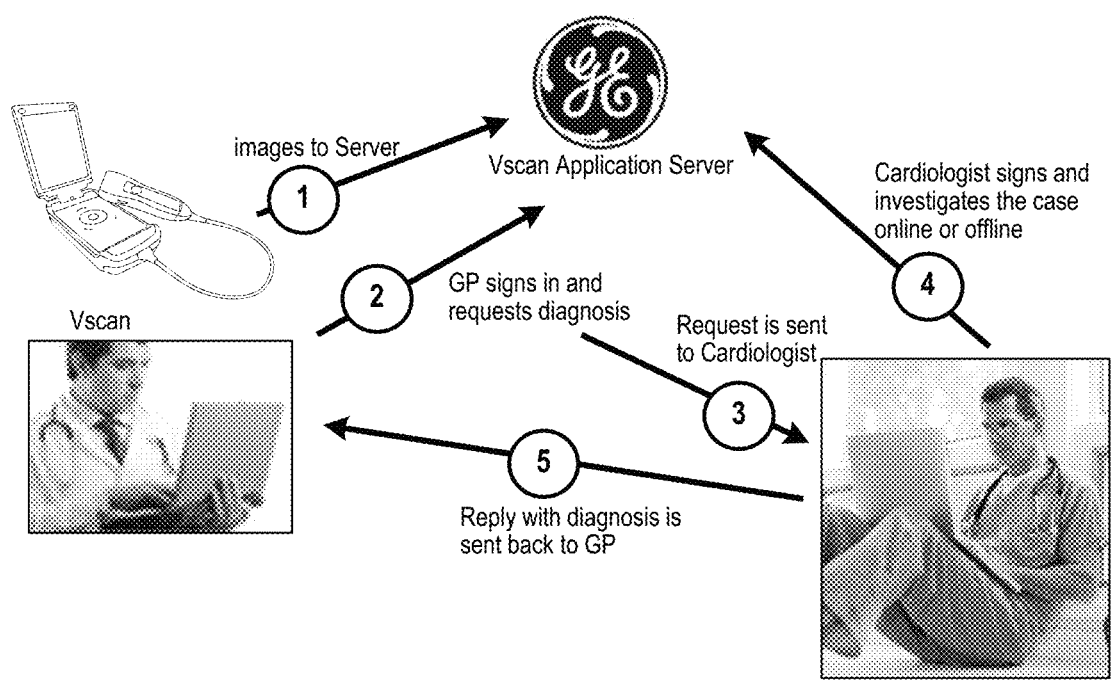
FIGS. 14 and 15 illustrate traditional workflows for medical image sharing in a primary care and emergency room setting.
Figure 15:
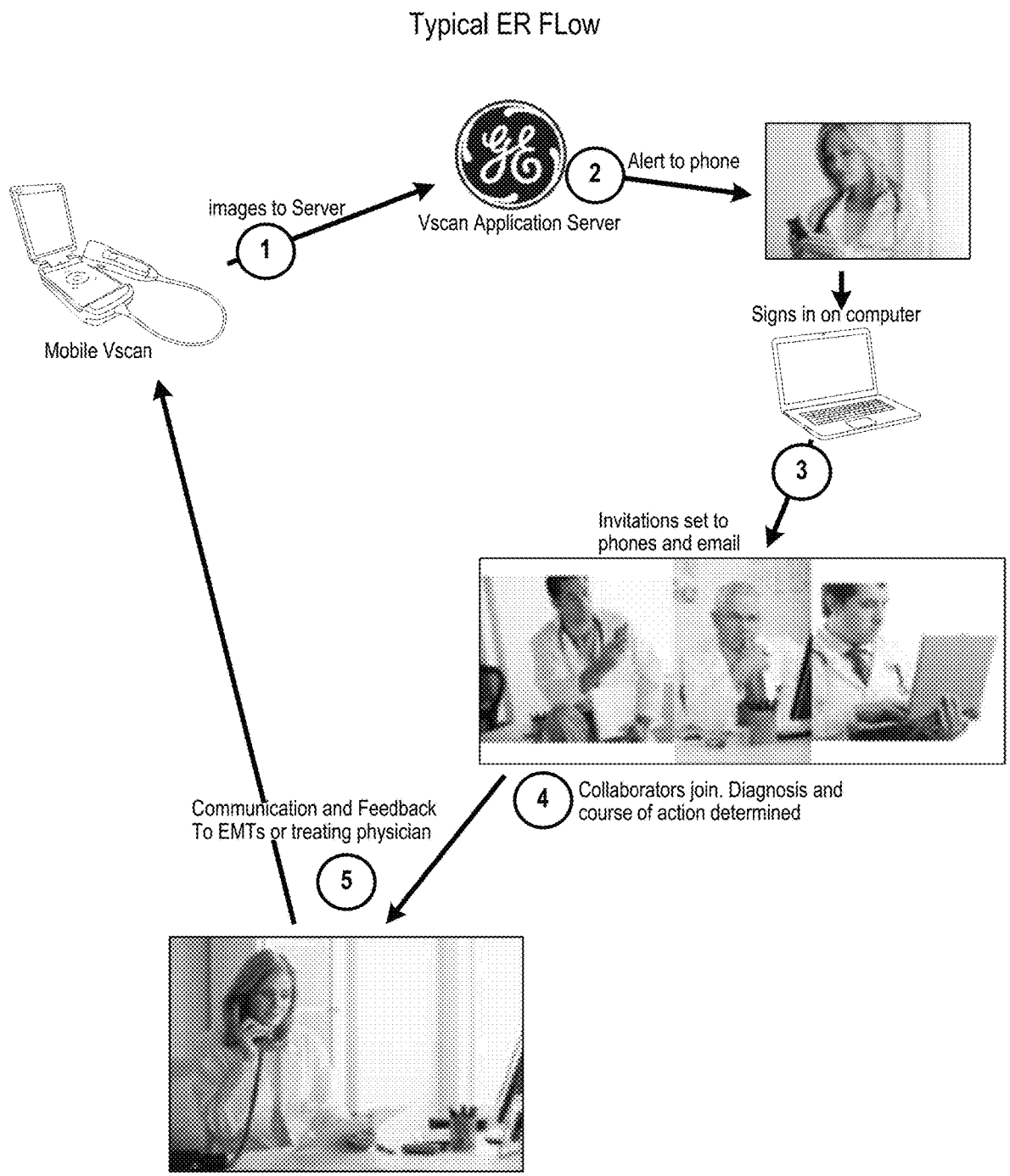

One embodiment of the encryption and conversion unit is illustrated in FIG. 13, where the encryption and conversion unit 104 acts as an encryption router to receive medical image files from one or more medical imaging devices 101 over a local network which may not be secure. The encryption and conversion unit 104 may be incorporated within each medical imaging device 101 as software, hardware or a combination of software and hardware. In another embodiment, the encryption and conversion unit 104 may be a part of a router, gateway, firewall or other network device which monitors and regulates traffic over a network. Regardless of the type of device in which it is placed, the encryption and conversion unit 104 will then be configured for encryption and conversion of a medical image into a secure and standardized image file format. The encryption and conversion unit 104 will then be configured for communication of the encrypted and/or converted image over a secure connection to a secure server 103 on a remote network, such as the Internet.

FIG. 12 illustrates a flowchart of the data flow of a medical image file from a local area network (LAN) 301 to a remote device on a remote wide area network (WAN) 307. The encryption and conversion unit 104 may include one or more of the components illustrated herein, either as software, hardware or a combination of both. In one embodiment, the encryption and conversion unit 104 includes an encryption listening port 302 which monitors network traffic in the LAN for the transmission of medical image files which are not encrypted or converted into a proper format. An encryption database 305 may store encryption settings that provide instructions on the type of encryption that a particular medical image file should be encrypted with, perhaps depending on the type of network or the destination device on the remote WAN network 307. The medical image file is processed 303 to encrypt the file, after which a port is mapped 304 for transmission of the file. The encrypted file is then transmitted through a firewall or other local router 306 to a remote WAN network 307.

In one example, a Vscan imaging device captures a medical image that is non-DICOM and not encrypted, but which is selected for transmission from the Vscan to a remote secure server on the remote network. The encryption and conversion unit 104 is embedded as software running on the Vscan device, and therefore converts the image to a DICOM image and encrypts the image before sending it out of the Vscan device to the remote secure server.

The encryption and conversion unit may be useful in a local network which is otherwise insecure or unreliable, as it creates a secure connection with the medical imaging devices and with a remotely connected server or device on another network. Additionally, the network device may be useful in highly secure networks with strict firewalls that would otherwise prevent connections to a remote secure server.

One embodiment provides a method and technical system for encrypting and routing DICOM network connections from devices without any such encryption capabilities built-in.

One embodiment of the invention can listen on known ports for unprotected communication and automatically encrypt and route the connection in its encrypted form over the port's encrypted counterpart. E.g. ordinary DICOM connections on TCP port 104 or 11112 can be encrypted in SSL/TLS and routed as DICOM/TLS on TCP port 2762. This would effectively make the connection appear to the remote server as a secure TLS connection and to the client device as an unprotected connection. By having the embodiment of the invention communicate with the network port of an imaging device or with a network router on the same protected local network as the device, a high level of security is maintained.

Likewise, ordinary "web" connections over the HTTP protocol on TCP port 80 can be encrypted in SSL/TLS and routed as HTTPS on TCP port 443. This would effectively make the connection appear to the HTTP server as a secure HTTPS connection and to the HTTP client as an unprotected connection. It should be noted here that encrypting HTTP traffic is useful only with older clients and servers which are capable of secure connections. It is, however, a well-known pair of network ports that serve to illustrate a general embodiment of the invention.

Embodiments of the invention include a wireless network connection such as WiFi or cellular modem capabilities to not only encrypt but also to offer access to the Internet without existing network infrastructure near the imaging device. This is highly useful for portable devices that can be used on-the-go running on battery power.

Embodiments of the invention can be pre-configured to only forward protected traffic to a single remote end-point. Embodiments of the invention may use any and all relevant encryption methods to secure the connection. Examples or these include the aforementioned SSL/TLS standard as well as other common encryption standards. The point being that the invention will mimic the native encryption standard for each type of connection an embodiment supports. Encryption may be encoded and decoded either by dedicated chips (electronic hardware components), software or a combination of software with hardware acceleration.

Integrating Image Management

Systems and methods for integrating a variety of communication protocols and file types relating to medical imaging are provided. The system integrates a current interface with third party software by adding software and intelligence to the current interface to provide for communication with third party image management software.

In one embodiment of the integration software, a medical imaging user interface such as a GE Viewpoint interface generates a plurality of medical images in a portable document format (PDF). The systems and methods described herein will then convert the PDF documents into DICOM formatted image documents, which may then be sent to a specific destination and then converted back into a PDF for viewing on an appropriate electronic device, such as a personal computer, portable electronic device, etc.

In another embodiment, an HL7 protocol device is used for medical software communication, and it includes a packet on the destination of a particular document. For example, an image created by an HL7 device needs to be sent to a doctor or patient. The integration software obtains information on the image, combines it with the command information on the destination for the image, and then adds it to a DICOM message.

The integration software works by obtaining information needed from the third party software system and determining information needed to convert, encrypt and send the images to the appropriate destination.

Real-Time Remote Interaction

The systems and methods described herein provide for live, or real-time, remote diagnosis of a medical problem of a patient using one or more medical images of the patient taken with a medical imaging device, such as an MM. The system may be embodied as a network with a plurality of computing and display devices which displays a graphical user interface (GUI) to each user so the users can all view the same medical images in real-time. The users are also provided with options to annotate the images in real-time, chat about the images through an instant messaging program and even talk using a voice-over-internet-protocol (VOIP) or a traditional landline conferencing system. The system provides a plurality of menus for a user to organize images, select diagnoses and other actions, and otherwise collaborate with a plurality of users in real-time to make a medical diagnosis based on one or more medical images.

Figure 16:
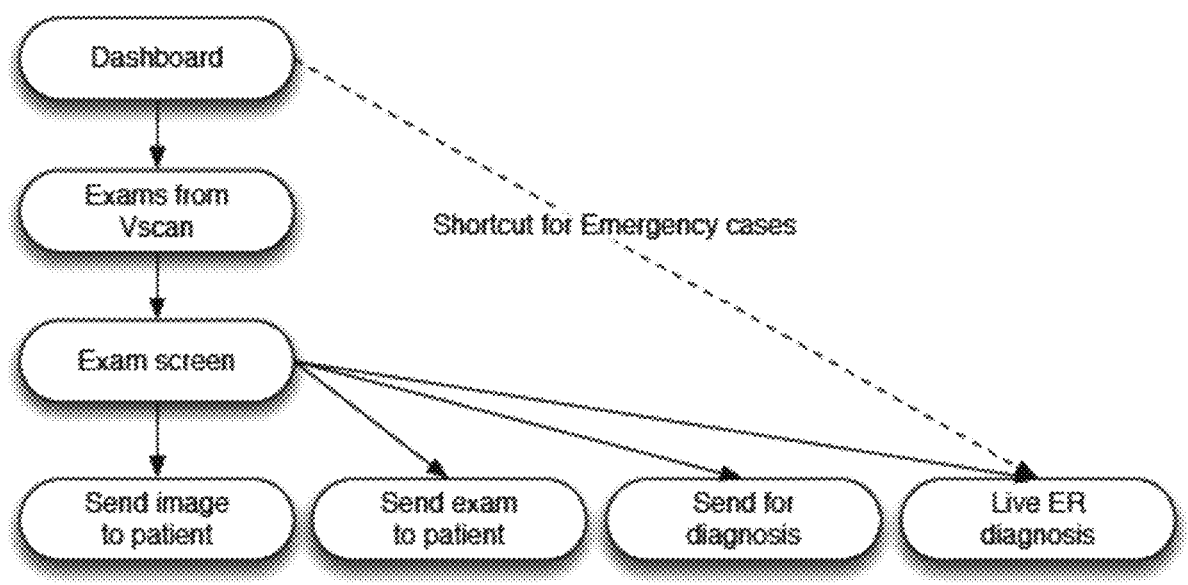
FIG. 16 is a flow chart of one embodiment of a system for real-time remote interactive collaboration for medical diagnoses.

FIG. 16 illustrates an overall workflow for the real-time remote interaction, where a user is first presented with a dashboard, or home screen, showing various options for collaborating to make a diagnosis. The dashboard is further illustrated in FIG. 18. Medical images from a Vscan device may be shown to the user, and an Exam Screen process may then be undertaken. During the exam screening, the images may be sent to a patient, an examination may be sent to the patient, and the resulting information may be sent for diagnosis. A live, or real-time, diagnosis may then be made. In a true emergency situation, the flowchart illustrates that these steps may be skipped in order to make an emergency diagnosis without collaborating with remote users.

Figure 17:
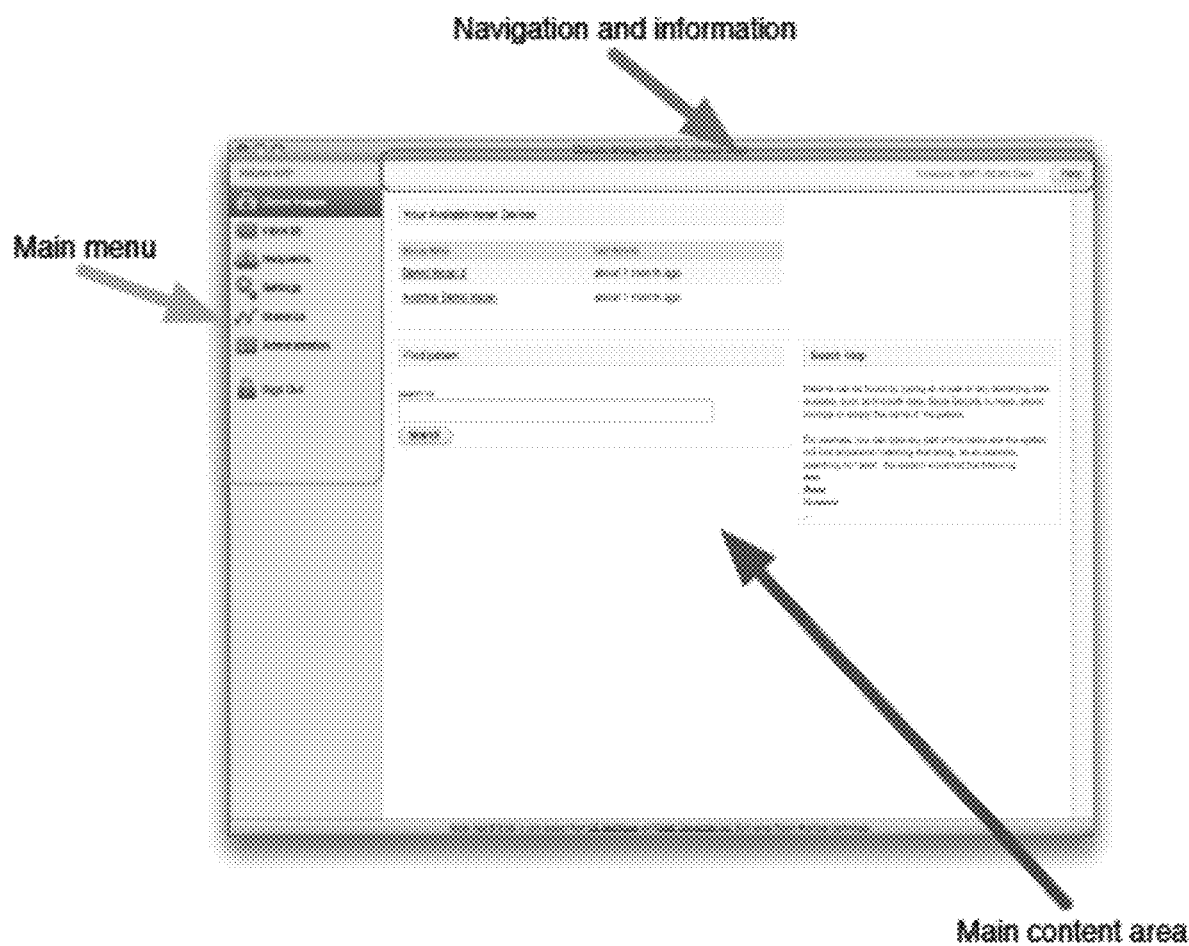
FIG. 17 illustrates a user interfaces which users of the real-time remote interaction system will view.

FIG. 17 illustrates an overall GUI which the user is presented with when viewing a display of a computing device on a network. A main menu, a main content area and a navigation and information section may all be provided.

FIG. 18 illustrates a "dashboard" GUI, which will list the medical imaging devices that are connected to the overall network or with the user's actual computing device (such as the medical imaging devices on the user's local network at a hospital or medical facility). The dashboard will also list the images that have been captured by those devices, and may arrange them in order of capture, by patient, by doctor, etc. If new images arrive, they may be moved to the top of the list and highlighted so the user can easily find them. In one embodiment, when a new image or images is captured by a particular device, an alert will go out to the appropriate physician or health care provider handling that patient's case—such as an SMS or e-mail message. The dashboard may also provide a search feature where the user can search through the images and a database of information related to the images and the patients.

FIG. 19 shows further detail of the main menu GUI, which provides: options to select DICOM images (where the main image workflows are found); and Inbox where the user will receive messages from the system or other users; a Recipients icon of patients or other users and contacts that can be easily found and contacted for sending images and messages; a Settings icon to handle setup of imaging devices, anonymization or automation of patient messages and labels to categorize studies; a Statistics icon to show traffic through the overall application over time; an Administration icon to show where administrators manage user accounts and setup branding of patient images; an Account icon where non-administrators can review their profiles and other account details; and a Sign Out icon that allows a user to sign out of the system. One will appreciate that the icons and options listed here are may be altered and are not limited to those described.

Figure 20:
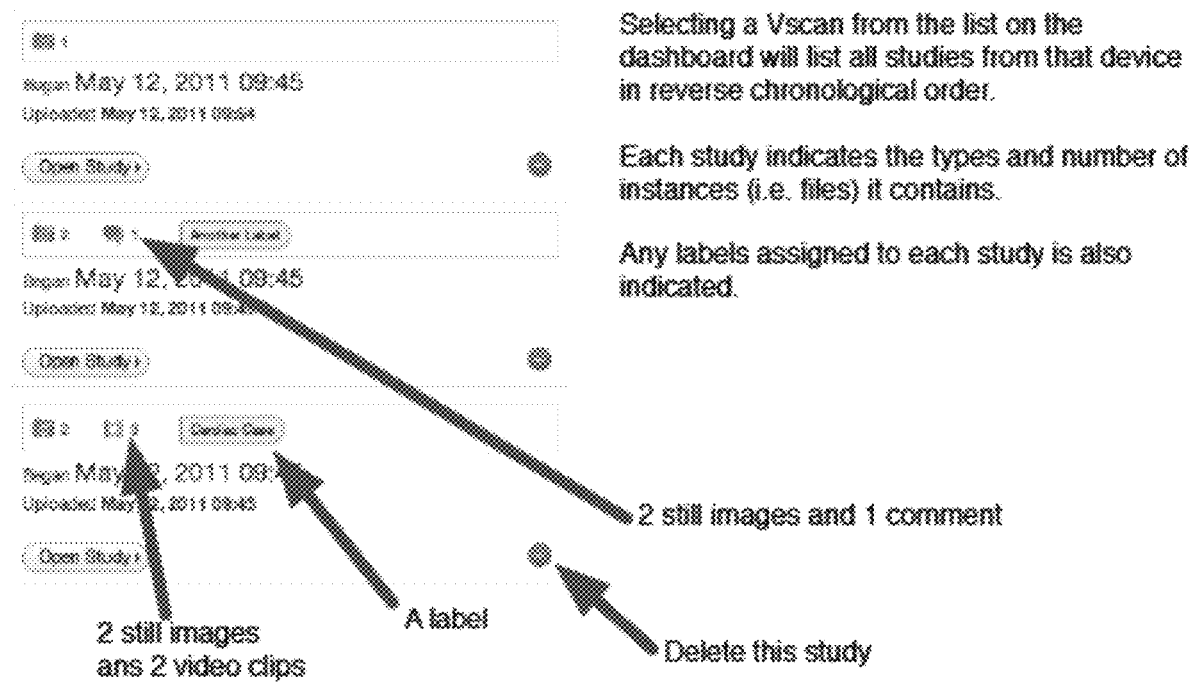
FIG. 20 illustrates a user interfaces which users of the real-time remote interaction system will view.

FIG. 20 illustrates one embodiment of an image workflow, where an image or a study of images can be selected from a list for further review. The study information may include the number of files and labels assigned to each study, as well as the number of comments made on particular studies and images by other users. Different icons for still images, videos, comments, etc. may be provided. The labels may pertain to suggested diagnoses or to a particular type of image or images contained within the study.

Figure 21:
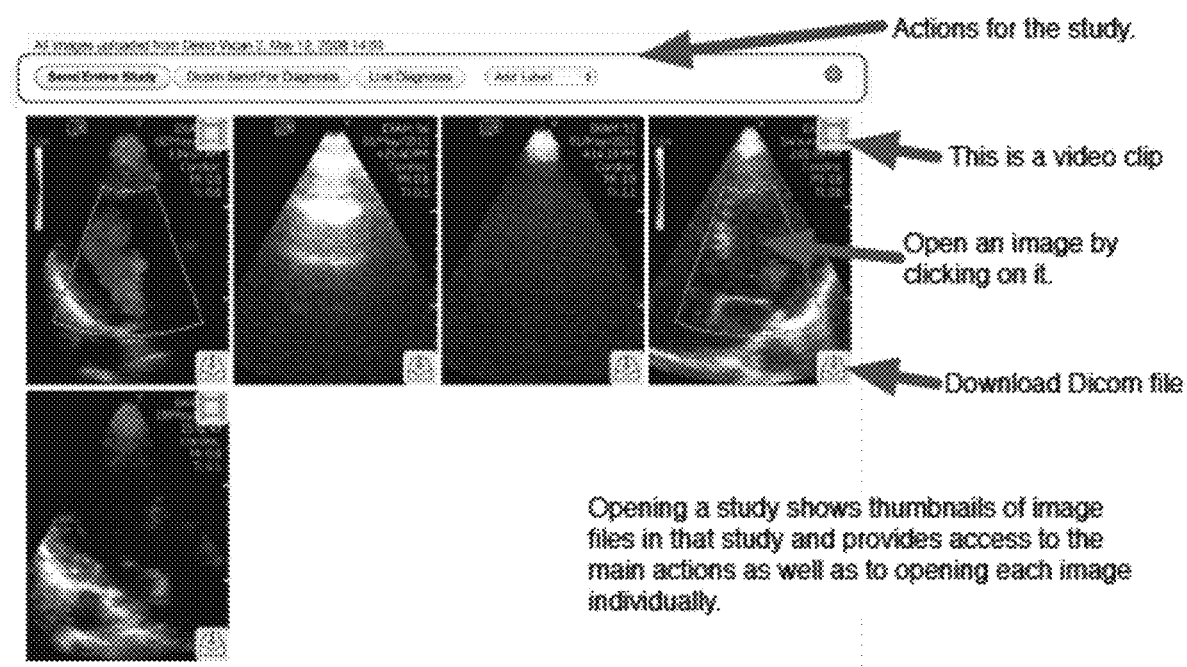
FIG. 21 illustrates a user interfaces which users of the real-time remote interaction system will view.

FIG. 21 illustrates a series of images as thumbnails that can be quickly reviewed before selecting one or more of them for further review. A list of actions is provided at the top of the GUI, and other icons on the thumbnails provide indications as to whether the thumbnail represents a video and whether it is of a particular image format (such as DICOM). The user may click or select one of the thumbnails to open the full image or video.

Figure 22:
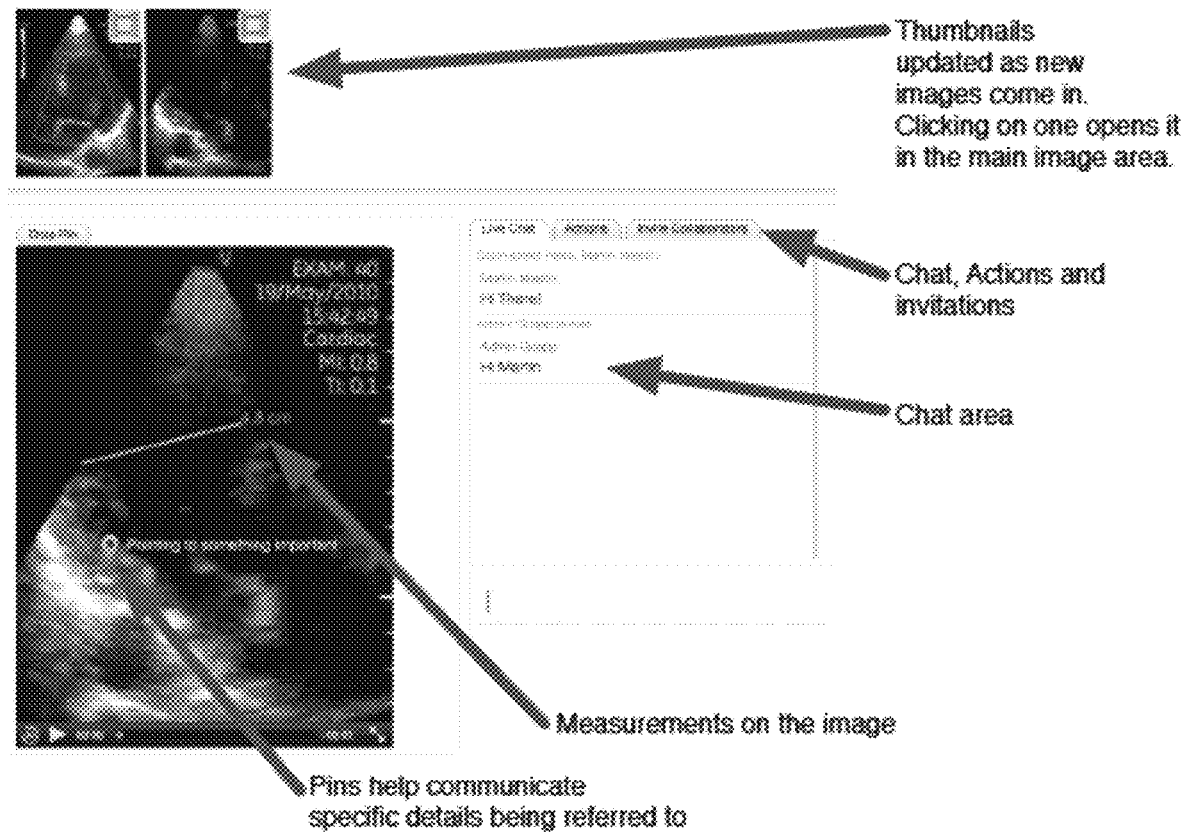
FIG. 22 illustrates a user interfaces which users of the real-time remote interaction system will view.

FIG. 22 is an illustration of a real-time remote interactive collaboration GUI, where a medical image is displayed along with annotations that are made on the image by one or more users. A chat screen is shown where the users can type instant messages to each other in the process of discussing the diagnosis of the patient, and a list of thumbnails of other images in the study may be provided at the top. The thumbnails may be updated as new images arrive. This "Live Diagnosis Screen" is a real-time collaboration tool that updates all information in real-time and synchronizes edits between users, including the annotations, chats, actions, selected images, pins and other changes. The live diagnosis screen may be particularly advantageous for an emergency room situation where a diagnosis is needed immediately. In the chat screen, the users have the option of inviting additional participants and taking one or more other actions related to the case.

Figure 23:
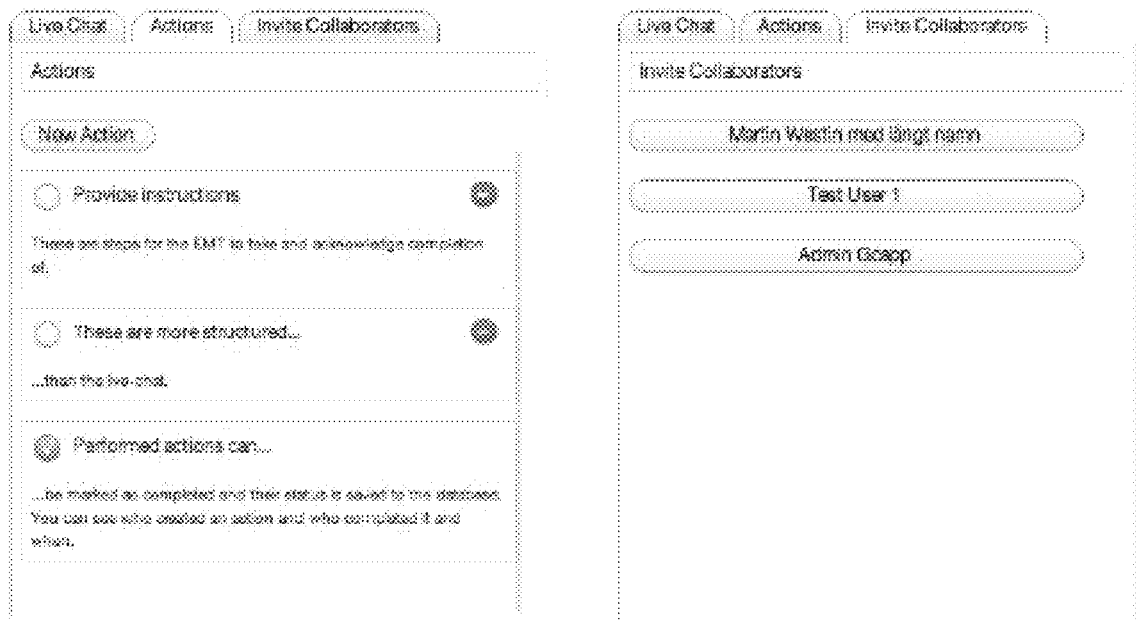
FIG. 23 illustrates a user interfaces which users of the real-time remote interaction system will view.

FIG. 23 illustrates one embodiment of the Actions that may be selected in the chat screen, and may be a way to provide unambiguous instructions to another user—such as a doctor or nurse who is providing care to the patient. The Actions tab may also provide tracking of the selected actions and who executed and suggested the actions so that the treatment of the patient can be properly documented. In the Invite Collaborators tab, a user can invite more users to participate in a live diagnosis process. The invited users may receive a text message, email or phone call asking them to join in the live chat session. The user interface may be adopted for any type of computing device, including mobile phones and tablets, to allow other users to participate from any location and with any type of portable electronic device.

FIG. 24 illustrates a GUI where a diagnosis can be requested for a particular patient based on a set of images. The user can select different options for concerns and possible diagnoses to be investigated. When the request is sent, one or more users may be informed via email, text or phone, and an inbox screen may be provided to show when replies arrive.

Figure 25:
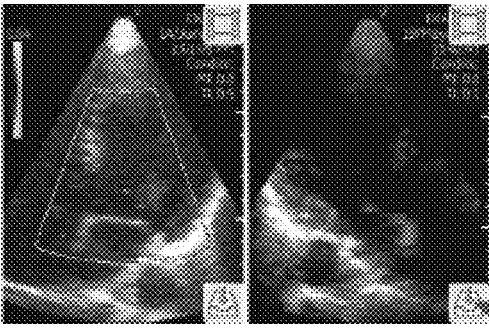
FIG. 25 illustrates a user interfaces which users of the real-time remote interaction system will view

In FIG. 25, the GUI for making a diagnosis is provided, where several images and a plurality of menus are provided to select appropriate diagnoses. The images may be downloaded to a computer desktop for more detailed viewing with other software tools. Options for potential diagnoses can be highlighted or selected. Once a final decision is reached, the diagnosis is sent and recorded in the record for future review and study.

What is claimed is:

1. A system comprising:
   a communication interface that communicates with at least one medical imaging device and at least one output destination;
   a memory storing one or more software modules; and
   at least one processor that executes the one or more software modules, stored in the memory, to perform a process comprising
   receiving unencrypted medical data from the at least one medical imaging device via the communication interface,
   converting the unencrypted medical data into a format that correlates with the at least one output destination to create converted unencrypted medical data,
   encrypting the converted unencrypted medical data to create encrypted medical data, and
   transmitting the encrypted medical data to the at least one output destination via the communication interface.

2. The system of claim 1, wherein the system comprises a dongle comprising the communication interface, the memory, and the at least one processor, wherein the dongle is physically attachable to a port of the at least one medical imaging device, and wherein the communication interface communicates with the at least one medical imaging device via physical attachment to the port.

3. The system of claim 2, wherein the communication interface communicates with the at least one output destination over a network.

4. The system of claim 3, wherein the communication interface provides the at least one medical imaging device with access to the network.

5. The system of claim 3, wherein the at least one output destination comprises a remote server.

6. The system of claim 3, wherein the communication interface communicates with the network via wireless communication.

7. The system of claim 6, wherein the network comprises a Wi-Fi network.

8. The system of claim 6, wherein the network comprises a cellular network.

9. The system of claim 1, wherein the at least one processor executes the one or more software modules to monitor all medical data generated by the at least one medical imaging device via the communication interface.

10. The system of claim 9, wherein the at least one processor executes the one or more software modules to, while monitoring the medical data generated by the at least one medical imaging device, whenever new unencrypted medical data is generated by the at least one medical imaging device, automatically perform the process for the new unencrypted medical data.

11. The system of claim 9, wherein monitoring comprises listening on at least one port for unencrypted medical data.

12. The system of claim 1, wherein the at least one output destination consists of a single output destination, such that the at least one processor transmits all encrypted medical data to only the single output destination.

13. The system of claim 1, wherein the unencrypted medical data comprises a Digital Imaging and Communications in Medicine (DICOM) file.

14. The system of claim 13, wherein the DICOM file comprises media content comprising one or more of an image or a video, and wherein converting the unencrypted medical data into the format that correlates with the at least one output destination comprises extracting the media content from the DICOM file, and converting the media content into a standard format that is compatible with the at least one output destination.

15. The system of claim 14, wherein converting the media content comprises reducing a resolution of the media content.

16. The system of claim 1, wherein the system comprises a network router comprising the communication interface, the memory, and the at least one processor, and wherein the communication interface communicates with the at least one medical imaging device over a private network, and communicates with the at least one output destination over a public network.

17. The system of claim 16, wherein the at least one processor executes the one or more software modules to:
monitor network traffic on the private network;
detect unencrypted medical data within the network traffic; and,
in response to each detection of unencrypted medical data, automatically perform the process for the detected unencrypted medical data.

18. The system of claim 1, wherein the one or more software modules comprise a software plug-in.

19. A method comprising using at least one processor to:
receive unencrypted medical data from at least one medical imaging device via a communication interface;
convert the unencrypted medical data into a format that correlates with at least one output destination to create converted unencrypted medical data;
encrypt the converted unencrypted medical data to create encrypted medical data; and
transmit the encrypted medical data to the at least one output destination via the communication interface.

20. A non-transitory computer-readable medium having instructions stored thereon, wherein the instructions, when executed by a processor, cause the processor to:
receive unencrypted medical data from at least one medical imaging device via a communication interface;
convert the unencrypted medical data into a format that correlates with at least one output destination to create converted unencrypted medical data;
encrypt the converted unencrypted medical data to create encrypted medical data; and
transmit the encrypted medical data to the at least one output destination via the communication interface.

* * * * *